US010563200B2

(12) United States Patent
Vainchenker et al.

(10) Patent No.: US 10,563,200 B2
(45) Date of Patent: *Feb. 18, 2020

(54) IDENTIFICATION OF A JAK2 MUTATION IN POLYCYTHEMIA VERA

(71) Applicants: Institut Gustave-Roussy, Villejuif (FR); Institut National de la Sante et de la Rescherche Medicale (INSERM), Paris (FR); Assistance Publique—Hopitaux de Paris, Paris (FR); Universite de Versailles—St Quentin en Yvelines, Versailles (FR); Universite Paris—Sud, Orsay (FR)

(72) Inventors: William Vainchenker, Paris (FR); Valerie Ugo, Brest (FR); Chloe James, Creon (FR); Jean-Pierre Le Couedic, Champs sur Marne (FR); Nicole Casadevall, Paris (FR)

(73) Assignees: ASSISTANCE PUBLIQUE—HOPITAUX DE PARIS, Paris (FR); INSTITUT NATIONAL DE LA SANTE DE LA RECHERCHE MEDICALE (INSERM), Paris (FR); INSTITUT GUSTAVE-ROUSSY, Villejuif (FR); UNIVERSITE DE VERSAILLES—ST QUENTIN EN YVELINES, Versailles (FR); UNIVERSITE PARIS—SUD, Orsay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/424,976

(22) Filed: May 29, 2019

(65) Prior Publication Data
US 2019/0323007 A1  Oct. 24, 2019

Related U.S. Application Data

(63) Continuation of application No. 14/164,880, filed on Jan. 27, 2014, now Pat. No. 10,364,430, which is a continuation of application No. 12/234,616, filed on Sep. 19, 2008, now Pat. No. 8,637,235, which is a continuation of application No. 11/934,359, filed on Nov. 2, 2007, now Pat. No. 7,429,456, which is a continuation of application No. 10/580,458, filed as application No. PCT/EP2005/055586 on Oct. 26, 2005, now Pat. No. 7,781,199.

(30) Foreign Application Priority Data

Oct. 27, 2004 (FR) .................................. 04 11480

(51) Int. Cl.
C12N 15/113 (2010.01)
G01N 33/574 (2006.01)
C12Q 1/6883 (2018.01)
C12Q 1/6813 (2018.01)
C12N 9/12 (2006.01)

(52) U.S. Cl.
CPC .......... C12N 15/113 (2013.01); C12N 9/1205 (2013.01); C12Q 1/6813 (2013.01); C12Q 1/6883 (2013.01); G01N 33/57426 (2013.01); G01N 33/57496 (2013.01); C12Q 2600/156 (2013.01); G01N 2333/91215 (2013.01); G01N 2500/04 (2013.01)

(58) Field of Classification Search
CPC combination set(s) only.
See application file for complete search history.

(56) References Cited

U.S. PATENT DOCUMENTS

| 5,747,282 | A  | 5/1998  | Skolnick et al. |
| 5,753,441 | A  | 5/1998  | Skolnick et al. |
| 5,914,393 | A  | 6/1999  | Coleman |
| 6,265,160 | B1 | 7/2001  | Leonard |
| 6,534,277 | B1 | 3/2003  | Hancock et al. |
| 6,582,908 | B2 | 6/2003  | Folor et al. |
| 6,821,724 | B1 | 11/2004 | Mittman et al. |
| 2003/0012788 | A1 | 1/2003 | Renauld et al. |
| 2004/0106132 | A1 | 6/2004 | Huang et al. |
| 2004/0205835 | A1 | 10/2004 | Ihle et al. |
| 2005/0235375 | A1 | 10/2005 | Chen |
| 2005/0250127 | A1 | 11/2005 | Fisher et al. |
| 2006/0019284 | A1 | 1/2006 | Huang et al. |
| 2006/0029944 | A1 | 2/2006 | Huang et al. |

(Continued)

FOREIGN PATENT DOCUMENTS

| EP | 1 186 672 B1 | 11/2005 |
| WO | WO 95/11995 | 4/1995 |

(Continued)

OTHER PUBLICATIONS

Baxter (The Lancet (2005) vol. 365, pp. 1054-1061).*
Top Scientists to Receive Prestigious Awards from the American Society of Hematology, Dec. 12, 2007, 2 pgs.
Andersson et al,. "No evidence for an altered nRNA expression or protein level of haematopoietic cell phosphatase in CD34+ bone marrow progenitor cells or mature peripheral blood cells in polycythaemia vera," Eur. J. Haematol., 1997, 59:310-317.
Arora et al., "Advances in molecular diagnostics of myeloproliferative disorders," Expert Opin. Med. Diagn., 2007, 1(1):65-80.

(Continued)

Primary Examiner — Steven Pohnert
(74) Attorney, Agent, or Firm — Potomac Law Group, PLLC

(57) ABSTRACT

The present invention concerns the V617F variant of the protein-tyrosine kinase JAK2, said variant being responsible for Vaquez Polyglobulia. The invention also relates to a first intention diagnostic method for erythrocytosis and thrombocytosis allowing their association with myeloproliferative disorders, or to the detection of the JAK2 V617F variant in myeloproliferative disorders allowing their reclassification in a new nosological group.

3 Claims, 11 Drawing Sheets

Specification includes a Sequence Listing.

(56) References Cited

U.S. PATENT DOCUMENTS

| | | |
|---|---|---|
| 2007/0111238 A1 | 5/2007 | Jamieson et al. |
| 2007/0248961 A1 | 10/2007 | Albitar et al. |
| 2013/0007927 A1 | 1/2013 | Copenhaver et al. |

FOREIGN PATENT DOCUMENTS

| | | |
|---|---|---|
| WO | WO 95/11995 A1 | 5/1995 |
| WO | WO 00/18960 A2 | 4/2000 |
| WO | WO 2004/063324 A2 | 7/2004 |

OTHER PUBLICATIONS

Asimakopoulos et al., "The gene encoding hematopoietic cell phosphatase (SHP-1) is structurally and transcriptionally intact in polycythemia vera," Oncogene, 1997, 14:1215-1222.

Barosi et al., "Incidence and Clinical Profile of JAK2 V617F Mutation in Myelofibrosis with Myeloid Metaplasia," Blood (ASH Annual Meeting Abstracts), Nov. 2005; 106(11):78a, Abstract 256.

Baxter et al., "The V617F JAK2 Mutation Is Uncommon in Cancers and Mutations in STAT5A, STAT5B and the JAK Family Genes Do Not Account for V617F Negative Myeloproliferative Disorders," Blood (ASH Annual Meeting Abstracts), Nov. 2005; 106(11):731a, Abstract 2598.

Berkofsky-Fessler et al., "The Transcriptional Profile of PV Displays Limited Similarity to EPO Stimulated Progenitor Cells: Evidence That JAK2 V617F Confers a Novel Program to Malignant Hematopoietic Stem Cells," Blood (ASH Annual Meeting Abstracts), Nov. 2005; 106(11):39a, Abstract 120.

Boggon, Titus J., "Jak3 Kinase Domain Crystal Structures and Implications for Jak-Specific Drug Design," Blood (ASH Annual Meeting Abstracts), Nov. 2005; 106(11):24a-25a, Abstract 69.

Bumm et al., "JAK2 V617F Mutation Induces a Myeloproliferative Disorder in Mice," Blood (ASH Annual Meeting Abstracts), Nov. 2005; 106(11):114a, Abstract 376.

Casadevall et al., "Erythroid Progenitors in Polycythemia Vera: Demonstration of Their Hypersensitivity to Erythropoeitin Using Serum Free Cultures," Blood, Feb. 1982, 59(2):447-451.

Cheung et al., "The Presence of the V617F Mutation Is Associated with Higher Haemoglobin, Older Age and an Increased Risk of Thrombosis in Essential Thrombocythemia," Blood (ASH Annual Meeting Abstracts), Nov. 2005; 106(11):985a, Abstract 3531.

Delhommeau et al., "Evidence that the JAK2 G1849T (V617F) mutation occurs in a lymphomyeloid progenitor in polycythemia vera and idiopathic myelofibrosis," Blood, Jan. 1, 2007, 109(1):71-77.

Ebert et al., "Characterization of Distinct Molecular Signatures in Myeloproliferative Diseases with the JAK2V617F Mutation and Wild Type JAK2," Blood (ASH Annual Meeting Abstracts), Nov. 2005; 106(11):39a, Abstract 119.

Falanga et al., "Distinct Hemostatic Profile of Leukocytes in Essential Thrombocythemia (ET) Carrying the JAK2 V617F Mutation," Blood (ASH Annual Meeting Abstracts), Nov. 2005; 106(11):114a, Abstract 378.

Finazzi et al. "JAKVal617Phe Mutation Correlates with the Risk of Thrombosis in Patients with Essential Thrombocythemia" Blood (ASH 47-Annual Meeting Abstract) 106: Abstract # 2580 Nov. 2005.

Fiorini et al. "Clonality Assay (X-CIP) and Jak2 V617P Mutation: Clustering Patients with Essential Thrombocythemia at High Risk for Thrombosis" Blood (ASH 47-Annual Meeting Abstract) 106: Abstract # 2597 Nov. 2005.

Gaikwad et al., "Will Imitanib Be Useful for Patients with Polycythemia Vera?", Blood (ASH Annual Meeting Abstracts), Nov. 2005; 106(11):731a-732a, Abstract 2601.

Garcon et al., Constitutive Activation of STAT5 and Bcl-XL Overexpression Can Induce Endogenous Erythroid Colony Formation in Human Primary Cells. Blood (ASH Annual Meeting Abstracts), Nov. 2005; 106(11):877a, Abstract 3135.

Gorre et al., "Novel Quantitative Flow Cytometry-Based Signaling Assays Reveal a Potential Role for HSP90 Inhibitors in the Treatment of JAK2 Mutant-Positive Diseases," Blood (ASH Annual Meeting Abstracts), Nov. 2005; 106(11):984a, Abstract 3526.

Green et al., "JAK2 V617F Mutation Identifies a Biologically Distinct Subtype of Essential Thrombocythemia Which Resembles Polycythemia Vera," Blood (ASH Annual Meeting Abstracts), Nov. 2005; 106(11):77a, Abstract 253.

Hess et al,. "Molecular analysis of the erythropoietin receptor system in patients with polycythaemia vera," British Journal of Maematology, 1994, 88:794-802.

IPSOGEN Cancer Profiler, JAK2 V617F MutaQuant™ Kit, 2008, 22 pgs.

James et al,. "Detection of JAK2 V617F in the Diagnosis of Erythrocytosis: Feasibility and Diagnostic Value in Clinical Practice," Blood (ASH Annual Meeting Abstracts), Nov. 2005; 106(11):703a, Abstract 2595.

Jamieson et al., "Molecular Progenitor Profiling in Human Myeloproliferative Disorders," Blood (ASH Annual Meeting Abstracts), Nov. 2005; 106(11):38a-39a, Abstract 118.

Jones et al., "No Significant Molecular Response in Polycythemia Vera Patients Treated with Imatinib or Interferon alpha," Blood (ASH Annual Meeting Abstracts), Nov. 2005; 106(11):113a, Abstract 373.

Kaushansky, Kenneth, "On the molecular origins of the chronic myeloproliferative disorders: it all makes sense," Blood, Jun. 1, 2005, 105(11):4187-4190.

Kaushansky, Kenneth, M.D., "The chronic myeloproliferative disorders and mutation of JAK2: Dameshek's 54 year old speculation comes of age," Best Practice & Research Clinical Haematology, 2007, 20(1):5-12.

Kiladjian et al., "Analysis of JAK2 Mutation in Essential Thrombocythemia (ET) Patients with Monoclonal and Polyclonal X-Chromosome Inactivation Patterns (XCIPs)," Blood (ASH Annual Meeting Abstracts), Nov. 2005; 106(11):732a, Abstract 2603.

Kiladjian et al., "Evidence for Pulmonary Vascular Disease Despite Absence of Overt Pulmonary Arterial Hypertension (PAH) in Myeloproliferative Disorders (MPD) (PV and ET)," Blood (ASH Annual Meeting Abstracts), Nov. 2005; 106(11):315b, Abstract 4939.

Kralovics et al., "Acquired uniparental disomy of chromosome 9p is a frequent step cell defect in polycythemia vera," Experimental Hematology, 2002, 30:229-236.

Le Bousse-Kerdiles et al. Members of the French Inserm GEM European EUMNET Networks, "Microarray Functional Comparison of CD34+ and Megakaryocytic Cell Transcriptomes in Myeloid Metaplasia with Myelofibrosis," Blood (ASH Annual Meeting Abstracts), Nov. 2005; 106(11):979a, Abstract 3505.

Le Couedic et al,. "Missense Mutation of the Erythropoietin Receptor Is a Rare Event in Human Erythroid Malignancies," Blood, Feb. 15, 1996, 87(4):1502-1511.

Lindauer et al., "Prediction of the structure of human Janus kinase 2 (JAK2) comprising the two carboxy-terminal domains reveals a mechanism for autoregulation," Protein Engineering, 2001, 14(1):27-37.

Lippert et al,. "The JAK-2-V617F mutation is frequently present at diagnosis in patients with essential thrombocythemia and polycythemia vera," Blood, Sep. 15, 2006, 108(6):1865-1867.

Marchetti et al. on Behalf of the Researchers of the Italian Registry of Myelofibrosis, "Clinical Classification of Myelofibrosis with Myeloid Metaplasia (MMM): Cluster Analysis of 861 Patients Enrolled into a Nationwide Prospective Registry (RIMM)," Blood (ASH Annual Meeting Abstracts), Nov. 2005; 106(11):725a, Abstract 2579.

Marcotegui et al., "A Gain of Function Mutation in JAK2 Is Frequently Found in Patients with AML-M2 and Normal Karyotype," Blood (ASH Annual Meeting Abstracts), Nov. 2005; 106(11):665a-666a, Abstract 2366.

May et al., "Generation of Specific Human CD8+ T Cell Responses to the Myeloproliferative Disorder Associated V617F Mutated JAK2 Kinase by Use of Analog Peptide Vaccine Candidates," Blood (ASH Annual Meeting Abstracts), Nov. 2005; 106(11):981a, Abstract 3512.

Means et al., "Erythropoietin Receptors in Polycythemia Vera," J. Clin, Inv., Oct. 1989, 84:1340-1344.

(56) References Cited

OTHER PUBLICATIONS

Mesa et al., "JAK2 (V617F) Mutation Status and Neutrophil Apoptotic Resistance in Myelofibrosis with Myeloid Metaplasia (MMM): Correlation and Potential Identification through Phosphorylation Status of Stats," Blood (ASH Annual Meeting Abstracts), Nov. 2005; 106(11):978a, Abstract 3503.

Mesa et al., "JAK2 V617F Mutational Status in Myelofibrosis at and before Disease Progression Including Leukemic Transformation: A Longitudinal Study in 68 Patients," Blood (ASH Annual Meeting Abstracts), Nov. 2005; 106(11):724a, Abstract 2575.

Moliterno et al., "Impaired expression of the thrombopoietin receptor by platelets from patients with polycythemia vera," The New England Journal of Medicine, Feb. 26, 1998, 572-580.

Moliterno et al., "Molecular Mimicry in the Chronic Myeloproliferative Disorders: Reciprocity between JAK2 V617F Genotype and Mpl Expression," Blood (ASH Annual Meeting Abstracts), Nov. 2005; 106(11):983a, Abstract 3520.

Moliterno et al., "Posttranslational Processing of the Thrombopoietin Receptor Is Impaired in Polycythemia Vera," Blood, Oct. 15, 1999, 94(8):2555-2561.

Ohyashiki et al., "Myelodysplastic Syndromes with Myelofibrosis May Be a Target for the JAK2 V617F Tyrosine Kinase Mutation," Blood (ASH Annual Meeting Abstracts), Nov. 2005; 106(11):304b, Abstract 4895.

Pardanani, A., "JAK2 inhibitor therapy in myeloproliferative disorders: rationale, preclinical studies and ongoing clinical trials," Leukemia, 2007, 1-8.

Passamonti et al., "Relationship between JAK2 V617F Mutation Status and Constitutive Mobilization of CD34-Positive Cells into Peripheral Blood in Patients with Chronic Myeloproliferative Disorder," Blood (ASH Annual Meeting Abstracts), Nov. 2005; 106(11):727a, Abstract 2586.

Patel et al., "Prevalence of the Activating JAK2 Tyrosine Kinase Mutation V617F in the Budd-Chiari Syndrome," Blood (ASH Annual Meeting Abstracts), Nov. 2005; 106(11):728a, Abstract 2588.

Pearson, Thomas C., "Evaluation of Diagnostic Criteria in Polycythemia Vera," Seminars in Hematology, Jan. 1, 2001, 38(1),Supp.2:21-24.

Percy et al., "Mutations in the VHL Gene Are the Major Identified Cause of Inherited Erythrocytosis," Blood (ASH Annual Meeting Abstracts), Nov. 2005; 106(11):169a, Abstract 569.

Pietra et al., "Relationship between JAK2 V617F Mutation Status, Granulocyte CD177 mRNA Expression and CD177 Soluble Protein Level in Patients with Polycythemia Vera," Blood (ASH Annual Meeting Abstracts), Nov. 2005; 106(11):725a, Abstract 2578.

Popat et al., "High Circulating CD34 Cells, Dacrocytes, Clonal Hematopoiesis, and JAK 2 Mutation Differentiate Secondary Myelofibrosis Associated with Pulmonary Hypertension from Myelofibrosis with Myeloid Metaplasia," Blood (ASH Annual Meeting Abstracts), Nov. 2005; 106(11):728a, Abstract 2589.

Potti et al., "Gene Expression Patterns Identify Novel Biologically Relevant Signaling and Transcriptional Pathways Involved in Terminal Erythroid Differentiation and Polycythemia Vera," Blood (ASH Annual Meeting Abstracts), Nov. 2005; 106(11):984a, Abstract 3524.

Prchal et al., "In Vitro Expansion of Polycythemia Vera Progenitors Favors Expansion of Erythroid Precursors without JAK2 V617F Mutation," Blood (ASH Annual Meeting Abstracts), Nov. 2005; 106(11):979a, Abstract 3506.

Quentmeier et al., "JAK2 V617F Tyrosine Kinase Mutation in Leukemia Cell Lines," Blood (ASH Annual Meeting Abstracts), Nov. 2005; 106(11):205b, Abstract 4505.

Roeder et al., "STAT3 is constitutively active in some patients with *Polycythemia rubra vera*," Experimental Hematology, 2001, 29:694-702.

Sattler et al., "The Jak2V617F Oncogene Associated with Polycythemia Vera Regulates G1/S-Phase Transition," Blood (ASH Annual Meeting Abstracts), Nov. 2005; 106(11):980a, Abstract 3510.

Schnittger et al., "JAK2 Mutation Screening and Chromosome Analysis Are Necessary for a Comprehensive Diagnostic Work up in CMPD: A Study on 469 Cases," Blood (ASH Annual Meeting Abstracts), Nov. 2005; 106(11):321b, Abstract 4963.

Silva et al., "Express of Bcl-x in erythroid precursors from patients with polycythemia vera," The New England Journal of Medicine, Feb. 26, 1998, 564-571.

Silver et al., "Validation of JAK2 and New Clinical Criteria for the Diagnosis of Polycythemia Vera (PV)," Blood (ASH Annual Meeting Abstracts), Nov. 2005; 106(11):323b, Abstract 4971.

Spivak et al., "Chronic Myeloproliferative Disorders," Hematology, 2003, 200-224.

Steensma, David P., "JAK2 V617F in Myeloid Disorders: Molecular Diagnostic Techniques and Their Clinical Utility," Journal of Molecular Diagnostics, Sep. 2006, 8(4):397-411.

Szpurka et al., "Presence of JAK2 Mutations in MDS/MPD-u WHO Classified Patients and Not Other Forms of MDS Suggests Their Derivation from Classical Myeloproliferative Syndrome," Blood (ASH Annual Meeting Abstracts), Nov. 2005; 106(11):112a, Abstract 369.

Tefferi et al,. "Classification and diagnosis of myeloproliferative neoplasms: The 2008 World Health Organization criteria and point-of-care diagnostic algorithms," Leukemia, 2008, 22:14-22.

Tefferi et al. "Concomitant Neutrophil JAK2V617F Mutation Screening and PRV-1 Expression Analysis in Myeloproliferative Disorders and Secondary Polycythaemia" British J. Hematology 131: 166-171 2005.

Tefferi et al., "The Clinical and PRV-1 Expression Phenotype of Wild-Type, Heterozygous, and Homozygous JAK2 V617F in Polycythemia Vera," Blood (ASH Annual Meeting Abstracts), Nov. 2005; 106(11):78a, Abstract 255.

Tefferi et al., "The JAK2(V617F) tyrosine kinase mutation in myelofibrosis with myeloid metaplasia: lineage specificity and clinical correlates," Br. J. Haematol., Nov. 2005, 131(3):320-8, Abstract two pages.

Tefferi et al., "Lenalidomide (CC-5013) Treatment for Anemia Associated with Myelofibrosis with Myeloid Metaplasia," Blood (ASH Annual Meeting Abstracts), Nov. 2005; 106(11):726a, Abstract 2583.

Tefferi et al., "The JAK2 V617F Tyrosine Kinase Mutation in Myelofibrosis with Myeloid Metaplasia: Clinical Correlates and Prognostic Relevance in 157 Patients," Blood (ASH Annual Meeting Abstracts), Nov. 2005; 106(11):978a, Abstract 3502.

Temerinac et al., "Cloning of PRV-1, a novel member of the uPAR receptor superfamily, which is overexpressed in polycythemia rubra vera," Blood, Apr. 15, 2000, 95(8):2569-2576.

Thurmes et al., "Molecularly Confirmed Polycythemia Vera with Elevated Endogenous Serum Erythropoietin Level: Diagnostic Algorithms Revisited," Blood (ASH Annual Meeting Abstracts), Nov. 2005; 106(11):321b-322b, Abstract 4964.

Vainchenker et al., "A Unique Activating Mutation in JAK2 (V617F) Is at the Origin of Polycythemia Vera and Allows a New Classification of Myeloproliferative Diseases," Hematology, Am Soc Hematol Educ Program. 2005,195-200.

Wolansky et al., "JAK2 V617F Mutation in Essential Thrombocythemia: Clinical Associations and Long-Term Prognostic Relevance," Blood (ASH Annual Meeting Abstracts), Nov. 2005; 106(11):77a-78a, Abstract 254.

Yoshida et al., "The JAK2 V617F Mutation Is Uncommon in Patients with Juvenile Myelomonocytic Leukemia," Blood (ASH Annual Meeting Abstracts), Nov. 2005; 106(11):316b, Abstract 4942.

Zaleskas et al., "Molecular Pathogenesis of Polycythemia Induced in Mice by JAK2 V617F," Blood (ASH Annual Meeting Abstracts), Nov. 2005; 106(11):38a, Abstract 116.

Zoi et al., "Increased Expression of the PRV-1 Gene in Thalassemia Reflects the Rate of the Underlying Erythropoietic Activity," Blood (ASH Annual Meeting Abstracts), Nov. 2005; 106(11):754a-755a, Abstract 2687.

NCBI Entrez, GenBank Report, Accession No. BV091334 (Oct. 15, 2003), http://www.ncbl.nlm.nlh.gov/nuccore/37668813, accessed on May 13, 2010.

Letter dated May 27, 2010 from Jorge Goldstein of Sterne Kessler Goldstein & Fox to Rouget Henschel of Foley & Lardner LLP.

(56) References Cited

OTHER PUBLICATIONS

Pahl, H. L:, "Towards a Molecular Understanding of Polycythemia Rubra Vera" European Journal of Biochemistry, Berlin, Germany, vol. 267, No. 12, Jun. 2000 (Jun. 2000), pp. 3395-3401, XP000982035 ISSN: 0014-2956.

JAK2 GeneCard (genecards.org/cgi-bin/carddisp.pl ?gene=JAK2 &search=jak2$suff=txt, Dec. 27, 2007, pp. 1-17.=).

Rossi et al., Leukemia Research, 2007, vol. 31, pp. 97-101.

Teffen et al., Leukemia Research, 2006, vol. 30, pp. 739-744.

James et al., "A unique clonal JAK2 mutation leading to constitutive signaling causes polycythaemia vera," Nature, vol. 434, No. 7037, Apr. 2005, pp. 1144-1148.

Notice of Allowance issued in U.S. Appl. No. 10/580,458 by the Examiner dated Apr. 6, 2010.

Notice of Allowance issued in U.S. Appl. No. 10/580,458 by the Examiner dated Jul. 9, 2010.

Database: N_Geneseq_200912, SEQ ID No. 3, 4, 11, 22, Mar. 2007 (first entry).

*Bio-Reference Laboratiories, Inc.*, Plaintiff v. *Ipsogen S.A. and Ipsogen, Inc.*, Defendants, United States District Court for the District of New Jersey, Civil Case No. 2:09-cv-06017-SRC-MAS, Complaint filed on Nov. 25, 2009.

*Bio-Reference Laboratories, Inc.*, Plaintiff v. *Assistance Publique— Hopitaux De Paris, et al.*, Defendants, United States District Court for the District of Columbia, Case No. 1:10-cv-00292-HHK, Complaint filed on Feb. 19, 2010.

Galye et al., "Identification of regions in interleukin-1 alpha important for activity," J. Biol. Chem., Oct. 15, 1993, vol. 268, No. 29, pp. 22105-22111.

Whisstock et al., "Prediction of protein function from protein sequence and structure," Q. Rev. Biophys., Aug. 2003, vol. 36, No. 3, pp. 307-340.

Kawamura et al., "Molecular cloning of L-JAK, a Janus family protein-tyrosine kinase expressed in natural killer cells and activated leukocytes," *Proc. Natl. Acad. Sci. USA*, Jul. 1994, vol. 14, pp. 6374-6378.

Blast USPTO in house alignment SEQ ID No. 1 vs. A55747 from Kawamura et al., 1994.

JAK2 Genecard (genecards.org/cgi-bin/carddisp.pl?gene=jak2&suff= txt) Dec. 27, 2007, pp. 1-7.

Office Action dated Apr. 20, 2009, by the Examiner in U.S. Appl. No. 10/580,458.

Office Action dated Oct. 2, 2008, by the Examiner in U.S. Appl. No. 10/580,458.

Office Action dated Feb. 21, 2008, by the Examiner in U.S. Appl. No. 10/580,458.

Notice of Allowance dated Aug. 12, 2008, by the Examiner in U.S. Appl. No. 11/934,359.

Office Action dated May 29, 2008, by the Examiner in U.S. Appl. No. 11/934,359.

Office Action dated Jan. 23, 2008, by the Examiner in U.S. Appl. No. 11/934,359.

Chloe, James, et al., "A unique clonal JAK2 mutation leading to constitutive signalling causes polycythaemia vera" Nature (London), vol. 434, No. 7037, Apr. 2005 (Apr. 2005), pp. 1144-1148, XP002369147 ISSN: 0028-0836.

Baxter, E. J., et al., The Cancer Genome Project "Acquired mutation of the tyrosine kinase JAK2 in human myeloproliferative disorders" Lancet The, Lancet Limited. London, GB, vol. 365, No. 9464, Mar. 19, 2005 (Mar. 19, 2005), pp. 1054-1061, XP004798459 ISSN: 0140-6.

Ugo, V., et al:, "Multiple signaling pathways are involved in erythropoietin-independent differentiation of erythroid progenitors in polycythemia vera" Experimental Hematology, New York, NY, US, vol. 32, No. 2, Feb. 2004 (Feb. 2004), pp. 179-187, XP002324352 ISSN: 0301-472X.

Saltzman, Alan, et al:, "Cloning and characterization of human Jak-2 kinase: High mRNA expression in immune cells and muscle tissue" Biochemical and Biophysical Research Communications, vol. 246, No. 3, May 29, 1998 (May 29, 1998), pp. 627-633, XP002324351 ISSN: 0006-291X.

Jones, A.V., et al., "Widespread Occurrence of the JAK2 V617F Mutation in chronic Myeloproliferative Disorders," Blood (Washington, DC) 106 (6): 2162-12168 (2005).

Levine, R. L., et al., "Activating Mutation in the Tyrosine Kinase JAK2 in Polycythemia Vera, Essential Thrombocythemia and Myeloid Metaplasia with Myelofibrosis," Cancer Cell. 2005; 7: 387-397.

Kralovics, R., et al., "A Gain-of-Function Mutation of JAK2 in Myeloproliferative Disorders," N Engl J Med 2005; 352:1779-1790, Apr. 28, 2005.

Zhao R., Xing S., Li Z., et al., Identification of an acquired JAK2 mutation in polycythemia vera. J Biol Chem 2005; 280:22788-92.

PCT/EP2005/055586, An International Search Report/Written Opinion (English Translation).

FR 200411480, Inpadoc report (Jul. 25, 2007).

FR 200411480, Derwent report (Jul. 25, 2007).

Database UniProt [Online] Jun. 7, 2005 (Jun. 7, 2005), "Janus kinase 2." XP002369149 extrait de EBI accession No. Uniprot:Q506Q0 Database accession No. 050600 Plus Commercial Vendor Search of (SEQ ID Nos. 1 and 3-12) summarized in a chart which contains a list of the alignments from DGENE, USGENE and Registry (PCTGEN and NCBI contained no unique results), by the STN accession number, the homology score, the assignee/corporate source, the title of the patent/article, the patent number/journal information, and the publication date.

Kiladjian, J. et al. "Analysis of JAK2 Mutation in Essential Thrombocythemia (ET) Patients with Monoclonal and Polyclonal X-Chromosome Inactivation Patterns (XCIPs)" Blood (ASH 47-Annual Meeting Abstract) 106: Abstract # 2603 Nov. 2005.

Fiorini, A. et al. "Clonality Assay (X-CIP) and Jak2 V617P Mutation: Clustering Patients with Essential Thrombocythemia at High Risk for Thrombosis" Blood (ASH 47-Annual Meeting Abstract) 106: Abstract # 2597 Nov. 2005.

Finazzi, G. et al. "JAKVaI617Phe Mutation Correlates with the Risk of Thrombosis in Patients with Essential Thrombocythemia" Blood (ASH 47-Annual Meeting Abstract) 106: Abstract # 2580 Nov. 2005.

Tefferi, A. et al. "Concomitant Neutrophil JAK2V617F Mutation Screening and PRV-1 Expression Analysis in Myeloproliferative Disorders and Secondary Polycythaemia" British J. Hematology 131: 166-171 2005.

Pearson et al., "Hemorheology in Erythrocytoses," Mt. Sinai J. Med., vol. 68, No. 3, pp. 182-191, May 2001.

Ding et al., "Familial Essential Thrombocythemia associated with a dominant-positive activating mutation of the c-MPL Gene, which encodes for the receptor for thrombopoietin," Blood, vol. 103, pp. 4198-4200, 2004.

Falanga et al., "V617F JAK-2 mutation in patients with essential thrombocythemia: relation to platelet, granulocyte, and plasma hemostatic and inflammatory molecules," Experimental Hematology, vol. 35, pp. 702-711, 2007.

Zhan et al., "The Diagnosis and Management of Polycythemia Vera, Essential Thrombocythemia, and Primary Myleofibrosis in the JAK2 V617F Era," Clinical Advances in Hematology and Onocology, vol. 7, pp. 334-342, 2009.

Kondo et al., "Familial Essential Thrombocythemia Associated with One-Based Deletion in the 5' Untranslated Region of the *Thrombopoietin* Gene," Blood, vol. 92, pp. 1091-1096, 1998.

Millecker et al., "Distinct patterns of cytogenetic and clinical progression in chronic myloproliferative neoplasms with or without JAK2 or MPL mutations," Cancer and Cytogenetics, vol. 197, pp. 1-7, 2010.

Ohashi et al., "Two rare MPL gene mutations in patients with essential thrombocythemia," Int. Journal of Hematology, vol. 90, pp. 431-432, 2009.

Idiopathic myleofibrosis (IM) bulletin, Leukemia and Lymphoma Society Bulletin, Sep. 2007.

GenBank accession No. NM004972.1, Gl:4826775 (Nov. 1, 2001).

Sambrook, Molecular Cloning—A Laboratory Manual, Second Edition, (Cold Spring Harbor Laboratory), 1999.

Landegren, Laboratory Protocols for Mutation Detection, (Oxford University Press), 1996.

(56) References Cited

OTHER PUBLICATIONS

Newton & Graham (PCR 2.nd edition, BIOS Scientific Publishers Limited) 1997.

Institute of Molecular Development (Molecular Techniques and Methods PCR Primers), p. 1, 2001.

ss 18852422 (http://www.ncbi.nim.nih.gov/SNP/snp_ss.cgl?subsnp_id=18852422) Feb. 20, 2004.

Vieux et al., "Primer Design for PCR and Sequencing in High-Throughput Analysis of SNPs," Biotechniques, vol. 32, pp. s28-s32, 2002.

Office Action issued in U.S. Appl. No. 12/234,616 dated Apr. 8, 2010.

Office Action issued in U.S. Appl. No. 12/234,616 dated Oct. 28, 2010.

Office Action issued in U.S. Appl. No. 12/234,616 dated Apr. 6, 2012.

Office Action issued in U.S. Appl. No. 12/234,616 dated Aug. 29, 2012.

Office Action issued in U.S. Appl. No. 12/234,616 dated Jan. 15, 2013.

Office Action issued in U.S. Appl. No. 12/234,616 dated Nov. 4, 2013.

Notice of Allowance issued in U.S. Appl. No. 12/234,616 dated Dec. 12, 2013.

International Search Report and Written Opinion issued in application No. PCT/EP2005/055586 dated Mar. 13, 2006.

"ipsogen JAK2 MutaScreen Kit Handbook", QIAGEN GmbH, Version 1, Mar. 2015, 60 pages.

Livak, Kenneth, "Allelic discrimination using fluorogenic probes and the 5' nuclease assay," Genetic Analysis: Bimolecular Engineering, vol. 14, 1999, pp. 143-149.

AY973034.1 (https://www.ncbl.nlm.nlh.gov/nuccore/62947929?Sat=11&satkey-3875884, May 3, 2005).

Vannucchi et al., "Prospective identification of high-risk polycythemia vera patients based on $JAK2^{v617F}$ allele burden," Leukemia, vol. 21, pp. 1952-1959, 2007.

Schwaller et al., "Stat5 is Essential for the Myelo- and Lymphoproliferative Disease Induced by TEL/JAK2," Molecular Cell, vol. 6, pp. 693-704, Sep. 2000.

Starmans-Kool et al., "An unwanted side effect of hydroxyurea in a patient with idiopathic myelofibrosis," Ann. Hematol., vol. 70, pp. 279-280, 1995.

\* cited by examiner

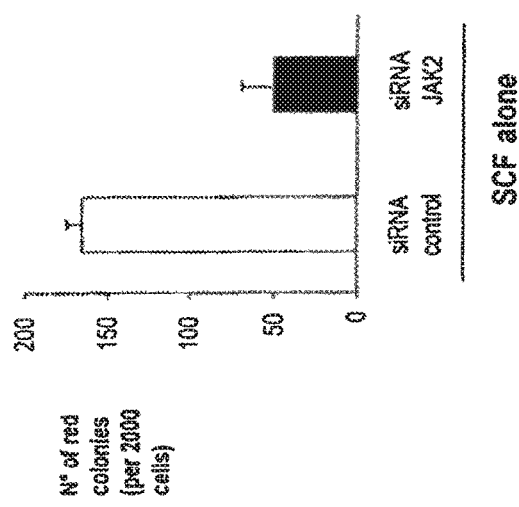
FIG. 5A
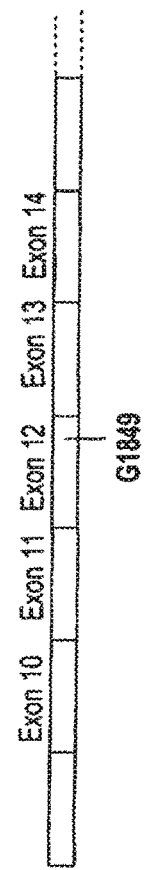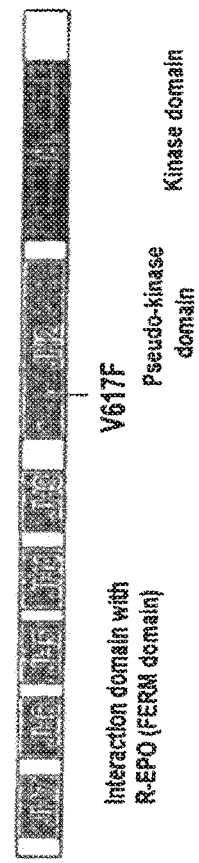
FIG. 5B sequences for V617F JAK2 of the siRNA #1, 2 and 3 position 11 = siRNA #3
position 10 = siRNA #1
position 9 = siRNA #4

(SEQ ID NO: 29) UGGAGUAUGUUUCUGUGGA
(SEQ ID NO: 30) GGAGUAUGUUUCUGUGGAG
(SEQ ID NO: 31) GAGUAUGUUUCUGUGGAGA

↑ Mutation

FIG. 8

SEQUENCE LISTING

<160> NUMBER OF SEQ ID NOS: 31

<210> SEQ ID NO 1
<211> LENGTH: 1132
<212> TYPE: PRT
<213> ORGANISM: homo sapiens
<220> FEATURE:
<223> OTHER INFORMATION: variant JAK2 V617F

<400> SEQUENCE: 1

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255
```

```
Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
            370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
            450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
            530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Lys Leu Ser His Lys His
            595                 600                 605

Leu Val Leu Asn Tyr Gly Val Cys Phe Cys Gly Asp Glu Asn Ile Leu
            610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670
```

-continued

Asn Val Cys Ala Lys Asn Ile Leu Leu Ile Arg Glu Glu Asp Arg Lys
            675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile

```
              1085                1090                1095
Tyr Met Ile Met Thr Glu Cys Trp Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 2
<211> LENGTH: 5097
<212> TYPE: DNA
<213> ORGANISM: homo sapiens
<220> FEATURE:
<223> OTHER INFORMATION: G1849T mutation in jak2 gene

<400> SEQUENCE: 2
```

| | | | | | |
|---|---|---|---|---|---|
| ctgcaggaag | gagagaggaa | gaggagcaga | aggggggcagc | agcggacgcc | gctaacggcc | 60 |
| tccctcggcg | ctgacaggct | gggccggcgc | ccggctcgct | tgggtgttcg | cgtcgccact | 120 |
| tcggcttctc | ggccggtcgg | gcccctcggc | ccgggcttgc | ggcgcgcgtc | ggggctgagg | 180 |
| gctgctgcgg | cgcagggaga | ggcctggtcc | tcgctgccga | gggatgtgag | tgggagctga | 240 |
| gcccacactg | gagggccccc | gagggcccag | cctggaggtc | gttcagagcc | gtgcccgccc | 300 |
| cggggcttcg | cagaccttga | cccgccgggt | aggagccgcc | cctgcgggct | cgagggcgcg | 360 |
| ctctggtcgc | ccgatctgtg | tagccggttt | cagaagcagg | caacaggaac | aagatgtgaa | 420 |
| ctgtttctct | tctgcagaaa | aagaggctct | tcctcctcct | cccgcgacgg | caaatgttct | 480 |
| gaaaaagact | ctgcatggga | atggcctgcc | ttacgatgac | agaaatggag | ggaacatcca | 540 |
| cctcttctat | atatcagaat | ggtgatattt | ctggaaatgc | caattctatg | aagcaaatag | 600 |
| atccagttct | tcaggtgtat | ctttaccatt | cccttgggaa | atctgaggca | gattatctga | 660 |
| cctttccatc | tggggagtat | gttgcagaag | aaatctgtat | tgctgcttct | aaagcttgtg | 720 |
| gtatcacacc | tgtgtatcat | aatatgtttg | ctttaatgag | tgaaacagaa | aggatctggt | 780 |
| atccacccaa | ccatgtcttc | catatagatg | agtcaaccag | gcataatgta | ctctacagaa | 840 |
| taagatttta | ctttcctcgt | tggtattgca | gtggcagcaa | cagagcctat | cggcatggaa | 900 |
| tatctcgagg | tgctgaagct | cctcttcttg | atgactttgt | catgtcttac | ctctttgctc | 960 |
| agtggcggca | tgattttgtg | cacgatgga | taaaagtacc | tgtgactcat | gaaacacagg | 1020 |
| aagaatgtct | tgggatggca | gtgttagata | tgatgagaat | agccaaagaa | aacgatcaaa | 1080 |
| ccccactggc | catctataac | tctatcagct | acaagacatt | cttaccaaaa | tgtattcgag | 1140 |
| caaagatcca | agactatcat | attttgacaa | ggaagcgaat | aaggtacaga | tttcgcagat | 1200 |
| ttattcagca | attcagccaa | tgcaaagcca | ctgccagaaa | cttgaaactt | aagtatctta | 1260 |
| taaatctgga | aactctgcag | tctgccttct | acacagagaa | atttgaagta | aaagaacctg | 1320 |
| gaagtggtcc | ttcaggtgag | gagattttg | caaccattat | aataactgga | aacgtggaa | 1380 |
| ttcagtggtc | aagagggaaa | cataaagaaa | gtgagacact | gacagaacag | gatttacagt | 1440 |
| tatattgcga | ttttcctaat | attattgatg | tcagtattaa | gcaagcaaac | caagagggtt | 1500 |
| caaatgaaag | ccgagttgta | actatccata | agcaagatgg | taaaaatctg | gaaattgaac | 1560 |
| ttagctcatt | aagggaagct | ttgtctttcg | tgtcattaat | tgatggatat | tatagattaa | 1620 |
| ctgcagatgc | acatcattac | ctctgtaaag | aagtagcacc | tccagccgtg | cttgaaaata | 1680 |
| tacaaagcaa | ctgtcatggc | ccaatttcga | tggattttgc | cattagtaaa | ctgaagaaag | 1740 |

```
caggtaatca gactggactg tatgtacttc gatgcagtcc taaggacttt aataaatatt    1800
ttttgacttt tgctgtcgag cgagaaaatg tcattgaata taaacactgt ttgattacaa    1860
aaaatgagaa tgaagagtac aacctcagtg ggacaaagaa gaacttcagc agtcttaaag    1920
atcttttgaa ttgttaccag atggaaactg ttcgctcaga caatataatt ttccagttta    1980
ctaaatgctg tcccccaaag ccaaaagata aatcaaacct tctagtcttc agaacgaatg    2040
gtgtttctga tgtaccaacc tcaccaacat tacagaggcc tactcatatg aaccaaatgg    2100
tgtttcacaa aatcagaaat gaagatttga tatttaatga aagccttggc caaggcactt    2160
ttacaaagat ttttaaaggc gtacgaagag aagtaggaga ctacggtcaa ctgcatgaaa    2220
cagaagttct tttaaaagtt ctggataaag cacacagaaa ctattcagag tctttctttg    2280
aagcagcaag tatgatgagc aagctttctc acaagcattt ggttttaaat tatggagtat    2340
gtttctgtgg agacgagaat attctggttc aggagtttgt aaaatttgga tcactagata    2400
catatctgaa aaagaataaa aattgtataa atatattatg gaaacttgaa gttgctaaac    2460
agttggcatg ggccatgcat tttctagaag aaaacaccct tattcatggg aatgtatgtg    2520
ccaaaaatat tctgcttatc agagaagaag acaggaagac aggaaatcct cctttcatca    2580
aacttagtga tcctggcatt agtattacag ttttgccaaa ggacattctt caggagagaa    2640
taccatgggt accacctgaa tgcattgaaa atcctaaaaa tttaaatttg gcaacagaca    2700
aatgagtttt tggtaccact ttgtgggaaa tctgcagtgg aggagataaa cctctaagtg    2760
ctctggattc tcaaagaaag ctacaatttt atgaagatag gcatcagctt cctgcaccaa    2820
agtgggcaga attagcaaac cttataaata attgtatgga ttatgaacca gatttcaggc    2880
cttctttcag agccatcata cgagatctta acagtttgtt tactccagat tatgaactat    2940
taacagaaaa tgcatgttta ccaaatatga ggataggtgc cctagggttt tctggtgcct    3000
ttgaagaccg ggatcctaca cagtttgaag agagacattt gaaatttcta cagcaacttg    3060
gcaagggtaa ttttgggagt gtggagatgt gccggtatga ccctctacag gacaacactg    3120
gggaggtggt cgctgtaaaa aagcttcagc atagtactga agagcaccta agagactttg    3180
aaagggaaat tgaaatcctg aaatccctac agcatgacaa cattgtaaag tacaagggag    3240
tgtgctacag tgctggtcgg cgtaatctaa aattaattat ggaatattta ccatatggaa    3300
gtttacgaga ctatcttcaa aaacataaag aacggataga tcacataaaa cttctgcagt    3360
acacatctca gatatgcaag ggtatggagt atcttggtac aaaaaggtat atccacaggg    3420
atctggcaac gagaaatata ttggtggaga acgagaacag agttaaaatt ggagattttg    3480
ggttaaccaa agtcttgcca caagacaaag aatactataa agtaaaagaa cctggtgaaa    3540
gtcccatatt ctggtatgct ccagaatcac tgacagagag caagttttct gtggcctcag    3600
atgtttggag ctttggagtg gttctgtatg aacttttcac atacattgag aagagtaaaa    3660
gtccaccagc ggaatttatg cgtatgattg gcaatgacaa acaaggacag atgatcgtgt    3720
tccatttgat agaacttttg aagaataatg gaagattacc aagaccagat ggatgcccag    3780
atgagatcta tatgatcatg acagaatgct ggaacaataa tgtaaatcaa cgcccctcct    3840
ttagggatct agctcttcga gtggatcaaa taagggataa catggctgga tgaaagaaat    3900
gaccttcatt ctgagaccaa agtagattta cagaacaaag ttttatattt cacattgctg    3960
tggactatta ttacatatat cattattata taaatcatga tgctagccag caaagatgtg    4020
aaaatatctg ctcaaaactt tcaaagttta gtaagttttt cttcatgagg ccaccagtaa    4080
aagacattaa tgagaattcc ttagcaagga ttttgtaaga agtttcttaa acattgtctg    4140
```

| | |
|---|---|
| ttaacatcac tcttgtctgg caaaagaaaa aaaatagact ttttcaactc agcttttga | 4200 |
| gacctgaaaa aattattatg taaattttgc aatgttaaag atgcacagaa tatgtatgta | 4260 |
| tagttttac cacagtggat gtataatacc ttggcatctt gtgtgatgtt ttacacacat | 4320 |
| gagggctggt gttcattaat actgttttct aattttcca tagttaatct ataattaatt | 4380 |
| acttcactat acaaacaaat taagatgttc agataattga ataagtacct ttgtgtcctt | 4440 |
| gttcatttat atcgctggcc agcattataa gcaggtgtat acttttagct tgtagttcca | 4500 |
| tgtactgtaa atattttca cataagggga acaaatgtct agtttatttt gtataggaaa | 4560 |
| tttccctgac cctaaataat acattttgaa atgaaacaag cttacaaaga tataatctat | 4620 |
| tttattatgg tttcccttgt atctatttgt ggtgaatgtg ttttttaaat ggaactatct | 4680 |
| ccaaattttt ctaagactac tatgaacagt tttcttttaa aatttgaga ttaagaatgc | 4740 |
| caggaatatt gtcatccttt gagctgctga ctgccaataa cattcttcga tctctgggat | 4800 |
| ttatgctcat gaactaaatt taagcttaag ccataaaata gattagattg tttttttaaaa | 4860 |
| atggatagct cattaagaag tgcagcaggt taagaatttt ttcctaaaga ctgtatattt | 4920 |
| gaggggtttc agaattttgc attgcagtca tagaagagat ttatttcctt tttagagggg | 4980 |
| aaatgaggta aataagtaaa aaagtatgct tgttaatttt attcaagaat gccagtagaa | 5040 |
| aattcataac gtgtatcttt aagaaaaatg agcatacatc ttaaatcttt tcaatta | 5097 |

<210> SEQ ID NO 3
<211> LENGTH: 554
<212> TYPE: DNA
<213> ORGANISM: homo sapiens
<220> FEATURE:
<223> OTHER INFORMATION: fragment of SEQ ID NO2 with the G1849T mutation

<400> SEQUENCE: 3

| | |
|---|---|
| ctcatatgaa ccaaatggtg tttcacaaaa tcagaaatga agatttgata tttaatgaaa | 60 |
| gccttggcca aggcactttt acaaagattt ttaaaggcgt acgaagagaa gtaggagact | 120 |
| acggtcaact gcatgaaaca gaagttcttt taaaagttct ggataaagca cacagaaact | 180 |
| attcagagtc tttctttgaa gcagcaagta tgatgagcaa gctttctcac aagcatttgg | 240 |
| ttttaaatta tggagtatgt ttctgtggag acgagaatat tctggttcag gagtttgtaa | 300 |
| aatttggatc actagataca tatctgaaaa agaataaaaa ttgtataaat atattatgga | 360 |
| aacttgaagt tgctaaacag ttggcatggg ccatgcattt tctagaagaa acacccctta | 420 |
| ttcatgggaa tgtatgtgcc aaaaatattc tgcttatcag agaagaagac aggaagacag | 480 |
| gaaatcctcc tttcatcaaa cttagtgatc ctggcattag tattacagtt ttgccaaagg | 540 |
| acattcttca ggag | 554 |

<210> SEQ ID NO 4
<211> LENGTH: 94
<212> TYPE: DNA
<213> ORGANISM: homo sapiens
<220> FEATURE:
<223> OTHER INFORMATION: fragment of SEQ ID NO3 with the G1849T mutation

<400> SEQUENCE: 4

| | |
|---|---|
| gatgagcaag ctttctcaca agcatttggt tttaaattat ggagtatgtt tctgtggaga | 60 |
| cgagaatatt ctggttcagg agtttgtaaa attt | 94 |

<210> SEQ ID NO 5

```
<211> LENGTH: 20
<212> TYPE: DNA
<213> ORGANISM: artificial sequence
<220> FEATURE:
<223> OTHER INFORMATION: PCR primer (54804-54823)

<400> SEQUENCE: 5
gggtttcctc agaacgttga                                              20

<210> SEQ ID NO 6
<211> LENGTH: 21
<212> TYPE: DNA
<213> ORGANISM: artificial sequence
<220> FEATURE:
<223> OTHER INFORMATION: PCR primer (55240-55260)

<400> SEQUENCE: 6
ttgctttcct ttttcacaag a                                            21

<210> SEQ ID NO 7
<211> LENGTH: 20
<212> TYPE: DNA
<213> ORGANISM: artificial sequence
<220> FEATURE:
<223> OTHER INFORMATION: sequencing primer (54813-54832)

<400> SEQUENCE: 7
cagaacgttg atggcagttg                                              20

<210> SEQ ID NO 8
<211> LENGTH: 27
<212> TYPE: DNA
<213> ORGANISM: artificial sequence
<220> FEATURE:
<223> OTHER INFORMATION: sequencing primer (55207-55233)

<400> SEQUENCE: 8
tgaatagtcc tacagtgttt tcagttt                                      27

<210> SEQ ID NO 9
<211> LENGTH: 21
<212> TYPE: DNA
<213> ORGANISM: artificial sequence
<220> FEATURE:
<223> OTHER INFORMATION: PCR and sequencing primer (1386-1407)

<400> SEQUENCE: 9
caacctcagt gggacaaaga a                                            21

<210> SEQ ID NO 10
<211> LENGTH: 23
<212> TYPE: DNA
<213> ORGANISM: artificial sequence
<220> FEATURE:
<223> OTHER INFORMATION: PCR and sequencing primer (2019-2041)

<400> SEQUENCE: 10
gcagaatatt tttggcacat aca                                          23

<210> SEQ ID NO 11
<211> LENGTH: 42
<212> TYPE: DNA
<213> ORGANISM: artificial sequence
<220> FEATURE:
<223> OTHER INFORMATION: SNPS probes and detection of mutation and siRNA
      (1829-1870)
```

```
<400> SEQUENCE: 11
ttttaaatta tggagtatgt gtctgtggag acgagaatat tc                          42

<210> SEQ ID NO 12
<211> LENGTH: 23
<212> TYPE: DNA
<213> ORGANISM: homo sapiens
<220> FEATURE:
<223> OTHER INFORMATION: sequence comprising the G1849T mutation

<400> SEQUENCE: 12
tatggagtat gtttctgtgg aga                                               23

<210> SEQ ID NO 13
<211> LENGTH: 21
<212> TYPE: DNA
<213> ORGANISM: homo sapiens
<220> FEATURE:
<221> NAME/KEY: misc_feature
<222> LOCATION: (20)..(21)
<223> OTHER INFORMATION: n is T
<220> FEATURE:
<223> OTHER INFORMATION: sense siRNA
<220> FEATURE:
<221> NAME/KEY: misc_feature
<222> LOCATION: (20)..(21)
<223> OTHER INFORMATION: DNA portion of combined DNA/RNA sequence

<400> SEQUENCE: 13
uggaguaugu uucguggan n                                                  21

<210> SEQ ID NO 14
<211> LENGTH: 21
<212> TYPE: DNA
<213> ORGANISM: homo sapiens
<220> FEATURE:
<221> NAME/KEY: misc_feature
<222> LOCATION: (20)..(21)
<223> OTHER INFORMATION: n is T
<220> FEATURE:
<223> OTHER INFORMATION: antisens siRNA
<220> FEATURE:
<221> NAME/KEY: misc_feature
<222> LOCATION: (20)..(21)
<223> OTHER INFORMATION: DNA portion of combined DNA/RNA sequence

<400> SEQUENCE: 14
uccacagaaa cauacuccan n                                                 21

<210> SEQ ID NO 15
<211> LENGTH: 21
<212> TYPE: DNA
<213> ORGANISM: artificial sequence
<220> FEATURE:
<223> OTHER INFORMATION: oligo "S" (sens)

<400> SEQUENCE: 15
ggcagagaga attttctgaa c                                                 21

<210> SEQ ID NO 16
<211> LENGTH: 21
<212> TYPE: DNA
<213> ORGANISM: artificial sequence
<220> FEATURE:
<223> OTHER INFORMATION: oligo "R" (antisens)

<400> SEQUENCE: 16
gctttccttt ttcacaagat a                                                 21
```

<210> SEQ ID NO 17
<211> LENGTH: 25
<212> TYPE: DNA
<213> ORGANISM: artificial sequence
<220> FEATURE:
<223> OTHER INFORMATION: "Sensor wt"

<400> SEQUENCE: 17
gtctccacag acacatactc cataa                                    25

<210> SEQ ID NO 18
<211> LENGTH: 25
<212> TYPE: DNA
<213> ORGANISM: artificial sequence
<220> FEATURE:
<223> OTHER INFORMATION: JAK2 primer

<400> SEQUENCE: 18
aaaaccaaat gcttgtgaga aagct                                    25

<210> SEQ ID NO 19
<211> LENGTH: 23
<212> TYPE: DNA
<213> ORGANISM: artificial sequence
<220> FEATURE:
<223> OTHER INFORMATION: cJAK2F

<400> SEQUENCE: 19
gcacacagaa actattcaga gtc                                      23

<210> SEQ ID NO 20
<211> LENGTH: 19
<212> TYPE: DNA
<213> ORGANISM: artificial sequence
<220> FEATURE:
<223> OTHER INFORMATION: cJAK2S

<400> SEQUENCE: 20
agcagcaagt atgatgagc                                           19

<210> SEQ ID NO 21
<211> LENGTH: 24
<212> TYPE: DNA
<213> ORGANISM: artificial sequence
<220> FEATURE:
<223> OTHER INFORMATION: cJAK2A

<400> SEQUENCE: 21
ctagtgatcc aaattttaca aact                                     24

<210> SEQ ID NO 22
<211> LENGTH: 21
<212> TYPE: DNA
<213> ORGANISM: artificial sequence
<220> FEATURE:
<223> OTHER INFORMATION: cJAK2R

<400> SEQUENCE: 22
gtttagcaac ttcaagtttc c                                        21

<210> SEQ ID NO 23
<211> LENGTH: 25
<212> TYPE: DNA
<213> ORGANISM: artificial sequence
<220> FEATURE:

<223> OTHER INFORMATION: "Sensor wt"

<400> SEQUENCE: 23
gtctccacag acacatactc cataa                                    25

<210> SEQ ID NO 24
<211> LENGTH: 25
<212> TYPE: DNA
<213> ORGANISM: artificial sequence
<220> FEATURE:
<223> OTHER INFORMATION: JAK2 primer

<400> SEQUENCE: 24
aaaaccaaat gcttgtgaga aagct                                    25

<210> SEQ ID NO 25
<211> LENGTH: 25
<212> TYPE: DNA
<213> ORGANISM: artificial sequence
<220> FEATURE:
<223> OTHER INFORMATION: sequence of sens primer

<400> SEQUENCE: 25
aagctttctc acaagcattt ggttt                                    25

<210> SEQ ID NO 26
<211> LENGTH: 26
<212> TYPE: DNA
<213> ORGANISM: artificial sequence
<220> FEATURE:
<223> OTHER INFORMATION: sequence of antisens primer

<400> SEQUENCE: 26
agaaaggcat tagaaagcct gtagtt                                   26

<210> SEQ ID NO 27
<211> LENGTH: 17
<212> TYPE: DNA
<213> ORGANISM: artificial sequence
<220> FEATURE:
<223> OTHER INFORMATION: sequence of "Reporter 1" (VIC)

<400> SEQUENCE: 27
tctccacaga cacatac                                             17

<210> SEQ ID NO 28
<211> LENGTH: 15
<212> TYPE: DNA
<213> ORGANISM: artificial sequence
<220> FEATURE:
<223> OTHER INFORMATION: sequence of "Reporter 2" (FAM)

<400> SEQUENCE: 28
tccacagaaa catac                                               15

<210> SEQ ID NO 29
<211> LENGTH: 19
<212> TYPE: RNA
<213> ORGANISM: artificial sequence
<220> FEATURE:
<223> OTHER INFORMATION: siRNA

<400> SEQUENCE: 29
uggaguaugu uucugugga                                           19

```
<210> SEQ ID NO 30
<211> LENGTH: 19
<212> TYPE: RNA
<213> ORGANISM: artificial sequence
<220> FEATURE:
<223> OTHER INFORMATION: siRNA

<400> SEQUENCE: 30
ggaguauguu ucuguggag                                                    19

<210> SEQ ID NO 31
<211> LENGTH: 19
<212> TYPE: RNA
<213> ORGANISM: artificial sequence
<220> FEATURE:
<223> OTHER INFORMATION: siRNA

<400> SEQUENCE: 31
gaguauguuu cuguggaga                                                    19
```

IDENTIFICATION OF A JAK2 MUTATION IN POLYCYTHEMIA VERA

The present invention concerns the V617F variant of the protein-tyrosine kinase JAK2, said variant being responsible for Vaquez Polyglobulia. The invention also relates to a first intention diagnostic method for erythrocytosis and thrombocytosis allowing their association with myeloproliferative disorders, or to the detection of the JAK2 V617F variant in myeloproliferative disorders allowing their reclassification in a new nosological group, and to the identification of specific inhibitors and siRNA.

Vaquez polyglobulia (Polycythemia Vera or PV) is a chronic myeloproliferative disorder associating true polyglobulia and, often, thrombocytosis and hyperleukocytosis. It is a clonal, acquired disease of the hematopoietic stem cell. The hematopoietic progenitors of PV are able to form erythroblast colonies in the absence of erythropoietin (Epo), called "spontaneous colonies". Hypersensitivity of PV erythroblast progenitors to several other growth factors has also been shown: Interleukin-3 (IL-3), Granulocyte Macrophage-Stimulating Factor (GM-CSF), Stem Cell Factor (SCF) and Insulin Like Growth Factor (IGF-1). Several teams have taken an interest in the physiopathology of PV, but the molecular anomaly at the root of the disease remains unknown to date (H.Pahl, 2000).

The hypersensitivity of PV progenitors to several cytokines leads to researching anomalies involving the signal transduction pathways common to cytokine receptors. The existence of a molecular marker has never been evidenced in PV, but given the similarities between PV and other myeloproliferative disorders, CML in particular, it appears probable that molecular mechanisms close to those induced by Ber-Ab1 are responsible for the predominant proliferation of the malignant clone and its end differentiation. This hypothesis was recently confirmed in two rare myeloproliferative disorders, the myeloproliferative disorders associated with a translocation involving the 8p11 chromosome region which induces constitutive activation of the FGF receptor, and the hypereosinophilic disorder in which a cryptic chromosome deletion leads to a chimeric gene PDGFRα-FIP1L1. In both cases, the molecular anomalies are the cause of fusion proteins having a constitutive tyrosine kinase activity.

In PV, no recurrent cytogenetic anomaly has been found, even if a 20 q deletion is detected in 10 to 15% of patients, and heterozygosity loss at 9 p in approximately 30% of cases (Kralovics, 2002). However, these anomalies are not specific to the disease.

Since PV cells are Epo-independent, research has been undertaken on the pathway of the Epo receptor (R-Epo). Firstly, the receptor is normal both structurally and functionally (Hess et al, 1994; Le Couedic et al, 1996; Means et al, 1989). The SHP-1 phosphatase which dephosphorylates R-Epo and JAK2 when Epo stimulation ceases, is normally expressed at RNA and protein level (Andersson et al, 1997; Asimakopoulos et al, 1997). Lower downstream in R-Epo signalling, abnormal activation of STAT5 has been researched in the polynuclear neutrophils (PNN) of patients presenting with PV but no anomaly has been found. On the other hand, constitutive phosphorylation of STAT3 has been evidenced in PNNs in 4 PV cases out of 14 examined (Roder, 2001). Finally, the expression of the anti-apoptotic protein bcl-xl, a transcriptional target of STAT5, has been studied in immunohistochemistry and by flow cytometry (Silva et al, 1998). It was shown that bcl-xl is hyperexpressed in PV erythroblasts, in particular at a more mature stage when this protein is normally no longer expressed.

In Vaquez polyglobulia, the chief diagnostic criteria to date are clinical (PVSG criteria: Pearson, 2001). Biological diagnosis is essentially based on growing cultures of erythroid progenitors in the absence of Epo (detection of endogenous colonies). On account of the necessary expertise for its proper conducting and the substantial "technician-time" required, this test is not available in every centre, and is only reliable when conducted by an experienced laboratory. In addition, the test requires medullary cells from the patient to obtain good sensitivity, which can be a tiresome procedure for the patient.

Using subtraction hybridising techniques, a German team has cloned a gene hyperexpressed in the PNNs of PV called PRV1 (Polycythemia *Rubra* vera 1) (Temerinac et al, 2000). The PRV-1 protein belongs to the superfamily of uPAR surface receptors. The hyperexpression of mRNA encoding PRV-1 in PV polynuclear neutrophils can be easily detected by real time RT-PCR; and forms a recently discovered marker of the disease, with no physiopathological role. However, recently published studies show that it is neither very sensitive nor very specific.

Spivak J L et al, in 2003 ("Chronic myeloproliferative disorders"; Hematology, 2003; 200 24) describes certain PV markers. The mRNAs of the neutrophilic antigen NBI/CD177 are overexpressed in the granulocytes of PV patients. This marker does not appear to be a reliable means however for detecting PV, some patients not showing this overexpression or this overexpression possibly being observed in patients suffering from myeloproliferative disorders other than Vaquez polyglobulia. Reduced expression of the thrombopoietin receptor, Mp1, on platelets is also found in PV. Although this anomaly is predominant in PV it is found in other myeloproliferative disorders. In addition, it is a test that is difficult to carry out and can only be performed in specialised laboratories.

Therefore, in the state of the art, no method exists which provides a reliable diagnosis of PV. In addition, the only available treatments are not specific. These relate to phlebotomy to maintain hematocrit within normal limits, or the use of cytotoxic agents or of IFN.

Under the present invention we have not only discovered a mutation in the JAK2 gene in approximately 90% of tested patients, but we have also evidenced that this mutation is responsible for constitutive activation of this tyrosine kinase and have shown that its inhibition makes it possible to block the spontaneous proliferation and differentiation of PV erythroblasts.

JAK2 belongs to the family of Janus Kinases (JAKs) which group together several intracytoplasmic tyrosine kinases: JAK1, JAK2, JAK3 and TYK2. The JAK proteins are involved in the intracellular signalling of numerous membrane receptors which have no intrinsic tyrosine kinase activity, like some members of the superfamily of cytokine receptors and in particular the Epo receptor (R-Epo). The JAK2 protein is encoded by a gene which comprises 23 exons. The size of the complementary DNA is 3500 base pairs and encodes a protein of 1132 amino acids (130 kD) (FIG. 1). Using PCR and sequencing we have identified a clonal, acquired, point mutation in exon 12 of JAK2 in nearly 90% of patients suffering from PV. The "GTC" 617 codon, normally coding for a Valine (V) is mutated to "TTC" coding for a Phenylalanine (F). This V617F mutation is not found in the 25 controls or patients suffering from secondary polyglobulia who were tested. On the other hand, it is found in 40% of essential thrombocytaemias and in 50% of myelofibroses, which means that this mutation defines a new myeloproliferative disorder framework in the same way as Bcr-Abl defined chronic myeloid leukaemia.

To examine whether the variant of the invention, JAK2 V617F, could be detected with efficacy using instruments given general wide use in haematology diagnostic laboratories, we analysed 119 samples from patients suspected of suffering from a myeloproliferative disorder. We have shown that JAK2 V617F is efficiently detected by LightCycler® and TaqMan® technologies, these being slightly more sensitive than sequencing. We then estimated the detection value of JAK2 V617F as first intention diagnostic test in 88 patients with hematocrit levels of over 51%, and it was shown that the mutation corresponded to PV diagnosis in accordance with WHO criteria (R=0.879) and PVSG criteria (R=0.717) with a positive predictive value of 100% in the context of erythrocytosis. On the basis of this data, we propose that the detection of JAK2 V617F in granulocytes should be considered as a first intention diagnostic test in patients with erythrocytosis, thereby avoiding the measurement of red cell mass, bone marrow procedure and in vitro analysis of the formation of endogenous erythroid colonies. This detection could also be extended in first intention to all myeloproliferative disorders or their suspected presence. This detection will be of particular importance for chronic thrombocytoses for which no certain biological tests exist to confirm a myeloproliferative disorder. It will also be an important test in the diagnosis of myelofibrosis and for clinical pictures associated with thromboses of undetermined aetiology.

Therefore, for the first time, the invention provides a diagnostic tool and opens the way to targeted treatment of PV and of myeloproliferative disorders associated with this mutation. More specifically, we propose the detection of the JAK2 V617F mutation as a first intention diagnostic test for erythrocytosis, making it possible to avoid quantification of red cell mass and erythroid endogenous colonies (EEC) as well as bone marrow testing in the majority of patients and in chronic thrombocytosis thereby avoiding lengthy aetiological search.

DESCRIPTION OF THE INVENTION

Therefore, according to a first characteristic, the present invention concerns the isolated protein JAK 2 (Janus kinase2), in particular the Homo sapiens Janus kinase2 protein (NCBI, accession number NM_004972; G1:13325062) comprising a mutation on amino acid 617 (codon 617 of the cDNA starting from ATG) more particularly the V617F mutation, hereinafter called variant JAK2 V617F such as presented in SEQ ID NO: 1 below:

```
(V617F Homo sapiens Janus kinase 2 or JAK2 V617F)
                                            SEQ ID NO: 1
MGMACLTMTEMEGTSTSSTYQNGDISGNANSMKQIDPVLQVYLYHSLGKSE

ADYLTFPSGEYVAEEICIAASKACGITPVYHNMFALMSETERIWYPPNHVF

HIDESTRHNVLYRIRFYFPRWYCSGSNRAYRHGISRGAEAPLLDDFVMSYL

FAQWRHDFVHGWIKVPVTHETQEECLGMAVLDMMRIAKENDQTPLATYNST

SYKTFLPKCIRAKIQDYHILTRKRIRYRFRRFIQQFSQCKATARNLKLKYL

INLETLQSAFYTEKFEVKEPGSGPSGEEIFATIIITGNGGIQWSRGKHKES

ETLTEQDLQLYCDFPNIIDVSIKQANQEGSNESRVVTIHKQDGKNLEIELS

SLREALSFVSLIDGYYRLTADAHHYLCKEVAPPAVLENIQSNCHGPISMDF
```
-continued
```
AISKLKKAGNQTGLYVLRCSPKDFNKYFLTFAVERENVIEYKHCLITKNEN

EEYNLSGTKKNESSLKDLLNCYQMETVRSDNIIFQFTKCCPPKPKDKSNLL

VFRTNGVSDVPTSPTLQRPTHMNQMVEHKIRNEDLIFNESLGQGTFTKIFK

GVRREVGDYGQLHETEVLLKVLDKAHRNYSESFFEAASMMSKLSHKHLVLN

YGVCF617CGDENILVQEFVKFGSLDTYLKKNKNCINILWKLEVAKQLAWA

MHFLEENTLIHGNVCAKNILLIREEDRKTGNPPFIKLSDPGISITVLPKDI

LQERIPWVPPECIENPKNLNLATDKWSFGTTLWEICSGGDKPLSALDSQRK

LQFYEDRHQLPAPKWAELANLINNCMDYEPDFRPSFRAIIRDLNSLFTPDY

ELLTENDMLPNMRIGALGFSGAFEDRDPTQFEERHLKFLQQLGKGNFGSVE

MCRYDPLQDNTGEVVAVKKLQHSTEEHLRDFEREIEILKSLQHDNIVKYKG

VCYSAGRRNLKLIMEYLPYGSLRDYLQKHKERIDHIKLLQYTSQICKGMEY

LGTKRYIHRDLATRNILVENENRVKIGDFGLTKVLPQDKEYYKVKEPGESP

IFWYAPESLTESKFSVASDVWSFGVVLYELFTYIEKSKSPPAEFMRMIGND

KQGQMIVFHLIELLKNNGRLPRPDGCPDEIYMIMTECWNNNVNQRPSFRDL

ALRVDQIRDNMAG
```

The invention also concerns equivalents of this protein mutated at position 617 in other mammals, for example JAK2 V617F in rat (NM_031514), porcine, murine (NM-008413) mammals . . . and variants of SEQ ID NO 1 which also comprise one or more alterations which do not affect the activity and 3D structure of the variant.

The invention also relates to a nucleotide sequence encoding SEQ ID NO: 1, preferably SEQ ID NO: 2 (sequence of the human JAK2 gene with the TTC codon instead of GTC on codon 617 (g/t mutation at position 1849 hereinafter called G1849T, starting from the ATG marking the start of translation).

This sequence may be found in a viral or plasmid vector, or a naked DNA under the control of a efficient promoter in mammalian cells. The invention therefore extends to a vector expressing the JAK2 V617F protein.

The vector of the invention may be a cloning and/or expression vector and may be used to transfect a host cell, in particular a mammalian cell, preferably a human CD34+ progenitor cell.

Model Transgenic Animal of PV and Other Myeloproliferative Disorders

The invention also concerns a non-human transgenic animal expressing recombinant JAK2 V617F. This animal may preferably be a mouse or rat. Transgenic rats or mice which can be used as models may be obtained by any method commonly used by those skilled in the art, in particular by a Knock-in method (targeted insertion of a sequence) by homologous recombination or directed recombination with the Cre-LoxP or FLP-FRT systems in ES cells. According to one preferred embodiment of the invention, the inventive transgenic cell is obtained by gene targeting of the JAK2 G1849T variant at one or more sequences of the host cell genome. More precisely, the transgene is inserted stable fashion by homologous recombination at the homologous sequences in the genome of the host cell. When it is desired to obtain a transgenic cell with a view to producing a transgenic animal, the host cell is preferably an embryonic stem cell (ES cell) (Thompson et al, 1989). Gene targeting is the directed modification of a chromosome locus by homologous recombination with an exogenous DNA sequence having sequence homology with the targeted endogenous sequence. There are different types of gene targeting. Here, gene targeting may be used more particularly to replace the wild-type JAK2 gene by the gene variant JAK2 G1849T or any other genetically similar variant. In this case, the gene targeting is called "Knock-in" (K-in). Alternatively, gene targeting may be used to reduce or annihilate expression of wild-type JAK2 to insert the gene of the JAK2 variant. This is then called "Knock-out" gene targeting (KO) (see Bolkey et al, 1989). The cell of the invention is characterized in that the transgene is integrated stably into the genome of said cell, and in that its expression is controlled by the regulatory elements of the endogenous gene. By stable integration is meant the insertion of the transgene into the genomic DNA of the inventive cell. The transgene so inserted is then transmitted to cell progeny. Integration of the transgene is made upstream, downstream or in the centre of the target JAK2 endogenous gene. Optionally, one or more positive or negative selection genes may be used. It is also possible to use DNA homology regions with the target locus, preferably a total of two, located either side of the reporter gene portion or either side of the complete sequence to be inserted. By "DNA homology regions" is meant two DNA sequences which, after optimal alignment and after comparison, are identical for usually at least approximately 90% to 95% of the nucleotides and preferably at least 98 to 99.5% of the nucleotides. Optimal alignment of the sequences for comparison may be made using the Smith-Waterman local homology algorithm (1981), the Neddleman-Wunsch local homology algorithm (1970), the similarity search method of Pearson and Lipman (1988), or computer software using these algorithms (GAP, BESTFIT, BLAST P, BLAST N, FASTA and TFASTA in the Wisconsin Genetics Software Package, Genetics Computer Group, 575 Science Dr., Madison, W1). Although as few as 14 bp with 100% homology are sufficient to achieve homologous recombination in bacteria and mammalian cells, longer portions of homologous sequences are preferred (in general the size of these portions is at least 2000 bp, preferably at least 5000 bp for each portion of homologous sequence. Advantageously, the JAK variant sequence is inserted in the group of elements ensuring endogenous type regulation, i.e. a group comprising at least the promoter, regulator sequences (enhancers, silencers, insulators) and the terminating signals of the endogenous JAK gene.

According to one particular embodiment, the transgene JAK G1849T comprises at least the encoding sequence, a positive selection cassette whether flanked or not by sites specific to the action of the recombinases, e.g. a Lox/Neo-TK/Lox cassette or lox/Neo/lox or FRT/Neo-TK/FRT ou FRT/Neo/FRT cassette possibly also being present at position 5' of said sequence, and characterized in that a negative selection cassette for example containing the DTA and/or TK gene or genes is at least present at one of the ends of the transgene. The transgene of the present invention is preferably directly derived from an exogenous DNA sequence naturally present in an animal cell. This DNA sequence in native form may be altered for example through the insertion of restriction sites needed for cloning and/or through the insertion of site-specific recombination sites (lox and flp sequences).

For this purpose, the JAK2 G1849T variant can be cloned in a cloning vector ensuring its propagation in a host cell, and/or optionally in an expression vector to ensure expression of the transgene. The recombinant DNA technologies used to construct the cloning and/or expression vector of the invention are known to those skilled in the art. Standard techniques are used for cloning, DNA isolation, amplification and purification; enzymatic reactions involving DNA ligase, DNA polymerase, restriction endonucleases are performed following the manufacturer's instructions. These techniques, and others are generally conducted in accordance with Sambrook et al, 1989. The vectors include plasmids, cosmids, bacteriophages, retroviruses and other animal viruses, artificial chromosomes such as YAC, BAC, HAC and other similar vectors.

The methods for generating transgenic cells of the invention are described in Gordon et al, 1989. Various techniques for transfecting mammalian cells were reviewed by Keon et al, 1990. The inventive transgene, optionally contained in a linearised or non-linearised vector, or in the form of a vector fragment, can be inserted in the host cell using standard methods such as microinjection into the nucleus for example (U.S. Pat. No. 4,873,191), transfection by calcium phosphate precipitation, lipofection, electroporation (Lo, 1983), heat shock, transformation with cationic polymers (PEG, polybrene, DEAE-Dextran.) or viral infection (Van der Putten et al, 1985).

When the cells have been transformed by the transgene, they may be cultured in vitro or else used to produce non-human transgenic animals. After transformation, the cells are seeded on a nutritional layer and/or in a suitable medium. The cells containing the construct can be detected using a selective medium. After a sufficient time to allow the colonies to grow, they are then collected and analysed to determine whether or not a homologous recombinant event and/or integration of the construct has occurred. To screen the clones possibly fulfilling homologous recombination, positive and negative markers, also called selection genes, may be inserted in the homologous recombination vector. Different systems for selecting cells producing the homologous recombination event have been described (for review U.S. Pat. No. 5,627,059). Said positive selection gene of the invention is preferably chosen from among antibiotic-resistant genes. Among the antibiotics a non-exhaustive list comprises neomycin, tetracycline, ampicilline kanamycin, phleomycin, bleomycin, hygromycin, chloramphenicol, carbenicilline, geneticine, puromycin. The resistance genes corresponding to these antibiotics are known to those skilled in the art; as an example the resistance gene to neomycin makes the cells resistant to the presence of the G418 antibiotic in the culture medium. The positive selection gene may also be chosen from among the HisD gene, the corresponding selective agent being histidinol. The positive selection gene may also be chosen from among the gene of guanine-phosphoribosyl-transferase (GpT), the corresponding selective agent being xanthine. The positive selection gene may also be chosen from among the hypoxanthine-phosphoribosyl-transferase gene(HPRT), the corresponding selective agent being hypoxanthine. The selection marker or markers used to allow identification of homologous recombination events may subsequently affect gene expression, and may be removed if necessary using specific site recombinases such as the Cre recombinase specific to Lox sites (Sauer, 1994; Rajewsky et al, 1996; Sauer, 1998) or FLP specific to FRT sites (Kilby et al, 1993).

The positive colonies, i.e. containing cells in which at least one homologous recombinant event has occurred, are identified by Southern blotting analysis and/or PCR techniques. The expression level, in the isolated cells or cells of the inventive transgenic animal, of the mRNA corresponding to the transgene may also be determined by techniques including Northern blotting analysis, in situ hybridisation analysis, by RT-PCR. Also, the cells or animal tissues expressing the transgene may be identified using an antibody directed against the reporter protein. The positive cells may then be used to conduct embryo handling procedures in particular the injection of cells modified by homologous recombination into the blastocysts.

Regarding mice, the blastocysts are obtained from 4 to 6-week superovulated females. The cells are trypsinated and the modified cells are injected into the blastocele of a blastocyst. After injection, the blastocysts are inserted into the uterine horn of pseudo-pregnant females. The females are then allowed to reach full term and the resulting offspring are analysed to determine the presence of mutant cells containing the construct. Analysis of a different phenotype between the cells of the newborn embryo and the cells of the blastocyst or ES cells makes it possible to detect chimeric newborn. The chimeric embryos are then raised to adult age. The chimera or chimeric animals are animals in which only a sub-population of cells contains an altered genome. Chimeric animals having the modified gene or genes are generally cross-bred between each other or with a wild-type animal to obtain either heterozygous or homozygous offspring. Male and female heterozygotes are then cross-bred to generate homozygous animals. Unless otherwise indicated, the non-human transgenic animal of the invention comprises stable changes in the nucleotide sequence of germ line cells.

According to another embodiment of the invention, the inventive non-human transgenic cell may be used as nucleus donor cell for the transfer of a nucleus, or nuclear transfer. By nuclear transfer is meant the transfer of a nucleus from a living donor cell of a vertebrate, an adult or foetal organism, into the cytoplasm of an enucleated receiver cell of the same species or a different species. The transferred nucleus is reprogrammed to direct the development of cloned embryos which can then be transferred to foster females to produce the foetuses and newborn, or can be used to produce cells of the inner cell mass in culture. Different nuclear cloning techniques may be used; among these, non-exhaustive mention may be made of those subject of patent applications WO 95 17500, WO 97/07668, WO 97 07669, WO 98 30683, WO 99 01163 and WO 99 37143.

Therefore, the invention also extends to a non-human transgenic animal comprising a recombinant sequence encoding JAK2 V617F. These animals may be homozygous or heterozygous (JAK2 V617F/JAK V617F or JAK2 V617F/JAK2). In particular, these animals reproduce Vaquez polyglobulia but also any myeloproliferative disorder induced by JAK2 V617F. They can therefore be used to conduct functional screening of tyrosine kinase inhibitors, especially screening of inhibitors specific to JAK2 V617F.

Another alternative consists of injecting a viral vector (retrovirus or lentivirus or others) able to express the JAK2 V617F variant in hematopoietic stem cells, progenitor cells or ES cells also with a view to producing models of Vaquez Polyglobulia or other myeloproliferative disorders.

Diagnostic Tools

According to a third characteristic, the invention relates to diagnostic tools with which to detect the presence or absence of the JAK2 V617F mutation in mammals suffering from or likely to show a myeloproliferative disorder, in particular in patients presenting with polyglobulia and who are suspected of having symptoms of Vaquez polyglobulia, thrombocytaemia and/or myelofibrosis.

In this respect, the invention relates to primers and probes with which to detect the presence or absence of the mutation in the SEQ ID NO: 2 sequence described above. More particularly, the invention pertains to an isolated nucleic acid having a sequence of at least 10, 12, 15, 20, 30, 40 or 50 consecutive nucleotides (e.g. 10 to 30 nucleotides or 10 to 25 nucleotides) of exon 12 or of the sequence SEQ ID NO: 3 or NO: 4 below and including the mutated $t^{1849}$ nucleotide, of 10 to 30 nucleotides for example.

```
                                           SEQ ID NO: 3
ctcatatgaaccaaatggtgtttcacaaaatcagaaatgaagatttgatat ttaatgaaagccttggccaaggcacttttacaaagattttttaaaggcgtac gaagagaagtaggagactacggtcaactgcatgaaacagaagttctttaa aagttctggataaagcacacagaaactattcagagtctttctttgaagcag caagtatgatgagcaagctttctcacaagcatttggttttaaattatggag tatgt$t^{1849}$tctgtggagacgagaatattctggttcaggagtttgtaaaattt ggatcactagatacatatctgaaaagaataaaaattgtataaatatatta tggaaacttgaagttgctaaacagttggcatgggccatgcattttctagaa gaaaacacccttattcatgggaatgtatgtgccaaaaatattctgcttatc agagaagaagacaggaagacaggaaatcctcctttcatcaaacttagtgat cctggcattagtattacagttttgccaaaggacattcttcaggag
```

The underlined sequence designates an example of upstream or downstream areas allowing the design of probes or primers specific to the mutation at position 1849 (SEQ ID NO: 4).

Example of Different Preferred Primers and Probes of the Invention.

```
On DNA, PCR PRIMERS:
JAK2EXON12-PCRF SENSE
                                       (SEQ ID NO: 5)
5'-GGGTTTCCTCAGAACGTTGA-3' (54804-54823)

JAK2EXON12-PCRR ANTI-SENSE
                                       (SEQ ID NO: 6)
5'-TTGCTTTCCTTTTTCACAAGA-3' (55240-55260)

ON DNA, SEQUENCING PRIMERS:
JAK2EXON12SEQF SENSE
                                       (SEQ ID NO: 7)
5'-CAGAACGTTGATGGCAGTTG-3' (54813-54832)

JAK2EXON12SEQR ANTI-SENSE
                                       (SEQ ID NO: 8)
5'-TGAATAGTCCTACAGTGTTTTCAGTTT-3' (55207-55233)

ON cDNA, PCR AND SEQUENCING PRIMERS
SENSE
                                       (SEQ ID NO: 9)
5'-CAACCTCAGTGGGACAAAGAA-3' (1386-1407)

ANTI-SENSE
                                       (SEQ ID NO: 10)
5'-GCAGAATATTTTTGGCACATACA-3' (2019-2041)

SNPS PROBES AND DETECTION OF MUTATION AND siRNA
(1829-1870):
                                       (SEQ ID NO: 11)
TTTTAAATTATGGAGTATGTGTCTGTGGAGACGAGAATATTC

GENOTYPING on LightCycler (DNA of PNN or marrow):
Oligo "S" (sense)
                                       (SEQ ID NO: 15)
GGCAGAGAGAATTTTCTGAAC Oligo "R" (anti-sense)
                                       (SEQ ID NO: 16)
GCTTTCCTTTTTCACAAGATA
```

-continued

Sensor wt
(SEQ ID NO: 17)
GTCTCCACAGACACATACTCCATAA 3'FL

Anchor JAK2
(SEQ ID NO: 18)
5'-LC Red640AAAACCAAATGCTTGTGAGAAAGCT 3'-PH

GENOTYPING on LightCycler (e.g. cDNA of platelets)
cJAK2F
(SEQ ID NO: 19)
GCACACAGAAACTATTCAGAGTC cJAK2S
(SEQ ID NO: 20)
AGCAGCAAGTATGATGAGC cJAK2A
(SEQ ID NO: 21)
CTAGTGATCCAAATTTTACAAACT cJAK2R
(SEQ ID NO: 22)
GTTTAGCAACTTCAAGTTTCC Sensor wt
(SEQ ID NO: 23)
GTCTCCACAGACACATACTCCATAA3'FL Anchor JAK2
(SEQ ID NO: 24)
5'-LC Red640AAAACCAAATGCTTGTGAGAAAGCT 3'-PH Genotyping Using TaqMan Technology (e.g. on DNA of Bone Marrow Mononuclear Cells).
Recognition using fluorescent probes specific to allele and single strand DNA.

PCR reaction
Primer sequence sense:
(SEQ ID NO: 25)
AAGCTTTCTCACAAGCATTTGGTTT

Primer sequence anti-sense:
(SEQ ID NO: 26)
AGAAAGGCATTAGAAAGCCTGTAGTT

Reporter 1 Sequence (VIC):
(SEQ ID NO: 27)
TCTCCACAGACACATAC

Reporter 2 Sequence (FAM):
(SEQ ID NO: 28)
TCCACAGAAACATAC.

According to further characteristic, the invention relates to an in vitro or ex vivo diagnostic method with which to detect the presence or absence of the JAK2 V617F mutation in a sample.

Tests with the Nucleic Acids of the Invention

Under a first embodiment, the G1849T variant (corresponding to the JAK2 V617F mutation) can be detected by analysis of the nucleic acid molecule of the JAK2 gene. Within the scope of the present invention, by "nucleic acid" is meant mRNA, genomic DNA or cDNA derived from mRNA.

The presence of absence of the nucleic acid of the G1849T variant can be detected by sequencing, amplification and/or hybridisation with a specific probe and specific primers such as described above: sequence derived from SEQ ID NO 3 or 4 and SEQ ID NO 5 to 11, or further SEQ ID NO 15 to 24.

The invention therefore proposes an ex vivo or in vitro method to determine the presence of absence of the G1849T variant of the JAK2 gene in a sample taken from a patient suffering from PV or likely to develop PV or any other myeloproliferative disorder, in particular erythrocytosis, thrombocytaemia and myelofibrosis disorders, the method comprising:

a) obtaining a nucleic acid sample from the patient,
b) detecting the presence or absence of the G1849T variant of the JAK2 gene in said nucleic acid sample.

characterized in that the presence of the G1849T variant is an indication of PV or any other myeloproliferative disorder.

The nucleic acid sample may be obtained from any cell source or tissue biopsy. These cells must be of hematopoietic origin and may be obtained from circulating blood, from hematopoietic tissue or any fluid contaminated with blood cells. The DNA can be extracted using any known method in the state of the art such as the methods described in Sambrook et al (1989). The RNA can also be isolated, for example from tissues obtained during a biopsy, using standard methods well known to those skilled in the art, such as extraction by guanidiumthiophenate-phenol-chloroform.

The G1849T variant of the JAK2 gene can be detected in a RNA or DNA sample, preferably after amplification For example, the isolated RNA can be subjected to reverse transcription followed by amplification, such as a RT-PCR reaction using oligonucleotides specific to the mutated site or which allow amplification of the region containing the mutation, for example exon 12 or sequence SEQ ID NO:3 or NO: 4. The expression "oligonucleotide" is used here to designate a nucleic acid of at least 10, preferably between 15 and 25 nucleotides, preferably less than 100 nucleotides, and which is able to hybridise to the genomic DNA of JAK2, to cDNA or to mRNA.

The oligonucleotides of the invention may be labelled using any technique known to those skilled in the art, such as radioactive, fluorescent or enzymatic labellers. A labelled oligonucleotide can be used as a probe to detect the presence or absence of the G1849T variant of the JAK2 gene.

Therefore, the probes and primers of use in the invention are those which hybridise specifically to the region of the JAK2 gene in the vicinity of the nucleotide at position 1849 (numbering as from the ATG marking the start of transcription).

In the above-explained method, the nucleic acids may be PCR amplified before detection of the allelic variation. The methods for detecting the allelic variation are described for example in "Molecular Cloning—A Laboratory Manual" Second Edition, Sambrook, Fritsch and Maniatis (Cold Spring Harbor Laboratory, 1989) and Laboratory Protocols for Mutation Detection, Ed. U. Landegren, Oxford University Press, 1996, and PCR $2^{nd}$ edition by Newton & Graham, BIOS Scientific Publishers Limited 1997.

In this respect it is possible to combine an amplification step followed by a detection step allowing discrimination between the samples in relation to the presence or absence of the sought variant.

Different techniques adapted for this purpose are described in EP 1 186 672 such as DNA sequencing, sequencing by SSCP, DGGE, TGGE hybridisation, heteroduplex analysis, CMC, enzymatic mismatch cleavage, hybridisation based solid phase hybridisation, DNA chips, Taqman™ hybridisation phase solution (U.S. Pat. Nos. 5,210,015 and 5,487,972) and the RFLP technique.

Detection can be conducted using different alternative methods: FRET, fluorescence quenching, polarised fluorescence, chemiluminescence, electro-chemiluminescence, radioactivity and colorimetry.

The method of the invention can include or exclude the steps consisting of obtaining the sample and extracting the nucleic acid from said sample.

As indicated above the sample used may be blood or any other body fluid or tissue obtained from an individual. After the nucleic acid extraction and purification steps, PCR amplification using the above-described primers can be used to improve signal detection.

Therefore, the method of the invention may comprise the amplification step with said primers, followed by a hybridisation step with at least one probe, preferably two probes which hybridise under conditions of high stringency to the sequences corresponding to the region of the G1849T mutation described above, and detection of the signal produced by the labellers of said probes.

For example, the invention particularly concerns an in vitro method to determine the presence or absence of the G1849T variant of the JAK2 gene in the sample of a patient with PV or likely to develop PV or any other myeloproliferative disorder, comprising the detection of the presence or absence of the G1849T variant of the JAK2 gene in said nucleic acid sample by means of one or SNPs (Single Nucleotide Polymorphism) specific to the G1849T mutation of the JAK2 gene, in particular SEQ ID NO 17, 18 or 23 and 24. characterized in that the presence of the G1849T variant is an indication of PV or of any other myeloproliferative disorder.

This detection by means of SNPs may be implemented using Taqman® Technology enabling allelic discrimination. Essentially, this method consists of the recognition, by the fluorescent probes specific to allele 1849, of JAK2 on single strand DNA and comprises a PCR reaction (with a polymerase with 5' exonuclease activity), detection of fluorescence emission specific to the allele of the hybridised SNPs, determination of the genotype by reading end point fluorescence (obtaining an image showing clusters of mutated homozygous, heterozygous and normal DNA).

Detection of the Mutated Protein JAK2 V617F

According to another embodiment, the variant can be detected directly within the JAK2 protein.

For this purpose, the invention concerns an ex vivo or in vitro method for detecting the presence or absence of the JAK2 V617F variant in a sample from a patient suffering from or likely to develop PV or any other myeloproliferative disorder, in particular erythrocytosis, thrombocytaemia and myelofibrosis, method consisting of:
a) obtaining a sample from the patient,
b) detecting the presence or absence of the JAK2 V617F variant, characterized in that the presence of said variant is an indication of PV or of any other myeloproliferative disorder.

Said JAK V617F variant can be detected by any suitable method known in the state of the art.

More particularly, a sample taken from an individual can be contacted with an antibody specific to the V617F variant of the JAK2 protein, e.g. an antibody which is able to distinguish between the V617F variant and the non-mutated JAK2 protein (and any other protein).

The antibodies of the present invention can be monoclonal or polyclonal antibodies, single chain or double chain, chimeric or humanised antibodies or portions of immunoglobulin molecules containing the portions known in the state of the art to correspond to the antigen binding fragments [human fragment, human F(ab')2 and F(v)].

These antibodies may be immunoconjugated, for example with a toxin or a marker.

The protocols for obtaining polyclonal antibodies are well known to those skilled in the art. Typically, said antibodies can be obtained by administering the JAK2 V617F variant via subcutaneous injection into white New Zealand rabbits previously prepared to obtain a pre-immunity serum. The antigens can be injected up to 100 µl per site at 6 different sites. The rabbits are prepared two weeks before the first injection, then periodically stimulated with the same antigen approximately three times every six weeks. A serum sample is then obtained ten days after each injection. The polyclonal antibodies are then purified of the serum by affinity chromatography using the JAK2 V617F protein to capture the antibodies.

Monoclonal antibodies are preferred to polyclonal antibodies on account of their high specificity.

Obtaining said monoclonal antibodies is within the reach of persons skilled in the art bearing in mind that the JAK2 V617F variant has a different 3D structure to the wild-type JAK2 protein. The expression "monoclonal antibody" means an antibody which is able to recognize only an epitope of an antigen.

Monoclonal antibodies can be prepared by immunizing a mammal, e.g. a mouse, rat or other mammals with the purified JAK2 V617F variant. The cells of the immunised mammal producing the antibodies are isolated and fused with the cells of myelomas or hetero-myelomas to produce hybrid cells (hybridomas).

The hybridoma cells producing the monoclonal antibody are used as production source for the antibody. The techniques for generating antibodies which do not involve immunisation are also concerned by the invention. For example "phage display" technology.

The antibodies directed against the JAK2 V617F variant may in some cases show a cross reaction with the wild-type JAK2 protein. If this is the case, a selection of the antibodies specific to the V617F variant is required. In this respect affinity chromatography may be used for example with the wild-type JAK2 protein to capture the antibodies showing a cross reaction with wild-type JAK2.

Therefore, the invention relates to a monoclonal antibody specifically recognizing the JAK2 V617F variant and to the hybridoma lines producing the antibody.

The invention also concerns an ELISA test using said antibody to detect the presence or absence of the JAK2 V617F variant in a sample.

One alternative to the use of antibodies may for example consist of preparing and identifying haptamers which are classes of molecules enabling specific molecular recognition.

Haptamers are oligonucleotides or oligopeptides which can virtually recognize any class of targeted molecules with high affinity and specificity.

Kits

According to another characteristic, the invention relates to kits to determine whether a patient is suffering from Vaquez polyglobulia or another myeloproliferative disorder involving the JAK2 V617F variant.

The inventive kit may contain one or more probes or primers such as defined above for the specific detection of the presence or absence of the G1849T mutation in the JAK2 gene.

The kit may also contain a heat-resistant polymerase for PCR amplification, one or more solutions for amplification and/or the hybridisation step, and any reagent with which to detect the marker.

According to another embodiment, the kit contains an antibody such as defined above.

The kits of the invention may also contain any reagent adapted for hybridisation or immunological reaction on a solid carrier.

The method and the detection kit are advantageously used for the sub-population of patients showing a hematocrit level higher than 51%. The method and the detection kit are also advantageously used for the sub-population of patients showing a platelet count of more than 450 000.

siRNA of the Invention

According to a fourth characteristic, the invention also relates to siRNAs enabling a reduction of more than 50%, 75%, 90%, 95% or more than 99% in the expression of JAK2 mutated at position 617, in particular JAK2 V617F. These siRNAs can be injected into the cells or tissues by lipofection, transduction or electroporation. They can be used to specifically destroy the mRNAs encoding JAK2 V617F thereby entailing numerous possible therapeutic applications, in particular the treatment of Vaquez polyglobulia.

srRNAs are described in U.S. 60/068,562 (CARNEGIE). The RNA is characterized in that it has a region with a double strand structure (ds). Inhibition is specific to the target sequence, the nucleotide sequence of one strand of the RNA ds region comprising at least 25 bases and being identical to the portion of the target gene. The nucleotide sequence of the other strand of the RNA ds region is complementary to that of the first strand and to the portion of the target gene. Also, application WO 02/44 321 (MIT/MAX PLANCK INSTITUTE) describes a double strand RNA (or oligonucleotides of same type, chemically synthesized) of which each strand has a length of 19 to 25 nucleotides and is capable of specifically inhibiting the post-transcriptional expression of a target gene via an RNA interference process in order to determine the function of a gene and to modulate this function in a cell or body. Finally, WO 00/44895 (BIOPHARMA) concerns a method for inhibiting the expression of a given target gene in a eukaryote cell in vitro, in which a dsRNA formed of two separate single strand RNAs is inserted into the cell, one strand of the dsRNA having a region complementary to the target gene, characterized in that the complementary region has at least 25 successive pairs of nucleotides. Persons skilled in the art may refer to the teaching contained in these documents to prepare the siRNAs of the invention.

More specifically, the invention relates to double strand RNAs of approximately 15 to 30 nucleotides, 19 to 25 nucleotides, or preferably around 19 nucleotides in length that are complementary (strand 1) and identical (strand 2) to sequence SEQ ID NO 3 comprising the G1849T mutation. These siRNAs of the invention may also comprise a dinucleotide TT or UU at the 3' end.

Numerous programmes are available for the design of the siRNAs of the invention:

"siSearch Program"
(Improved and automated prediction of effective siRNA", Chaml A M, Wahlesdelt C and Sonnhammer E L L, Biochemical and Biophysical research Communications, 2004).

"SiDirect"
(Direct: highly effective, target-specific siRNA design software for amammalian RNA interface, Yuki Naito et al. Nucleic Acids Res., Vol. 32, NO Web Server Issue© Oxford University Press, 2004).

"siRNA Target Finder" by Ambion.

"siRNA design tool" by Whitehead Institute of Biomedical research at the MIT.

Other programmes are available.

For example, for the sequence TATGGAGTATGTT[1849]TCTGTGGAGA (SEQ ID NO: 12) the sense siRNA is UGGAGUAUGUUUCUGUGGAdTdT (SEQ ID NO: 13) and the anti-sense siRNA is UCCACA-GAAACAUACUCCAdTdT (SEQ ID NO: 14).

In one particular embodiment, the siRNAs of the invention described above are tested and selected for their capability of reducing, even specifically blocking the expression of JAK2 VI617F, affecting as little as possible the expression of wild-type JAK2. For example, the invention concerns siRNAs allowing a reduction of more than 80%, 90%, 95% or 99% of the expression of JAK2 V617F and no reduction or a reduction of less than 50%, 25%, 15%, 10% or 5% or even 1% of wild-type JAK2.

For example, the siRNAs of the invention can be selected from the group consisting of:

```
UGGAGUAUGUUUCUGUGGA          (SEQ ID NO: 29)

GGAGUAUGUUUCUGUGGAG          (SEQ ID NO: 30)

GAGUAUGUUUCUGUGGAGA          (SEQ ID NO: 31)
```

According to another embodiment, the invention concerns a ddRNAi molecule such as described generic fashion in application WO 01/70949 (Benitec) but specifically targeting JAK2 V617F. The ddRNAi of the invention allows extinction of the sequence coding for JAK2 V617F and comprises (i) an identical sequence to SEQ ID NO 3, 4 or 11; (ii) a sequence complementary to the sequence defined under (i); (iii) an intron separating said sequences (i) and (ii); the introduction of this construct in a cell or tissue producing an RNA capable of altering the expression of JAK2 V617F.

The invention also relates to a genetically modified non-human animal comprising one or more cells containing a genetic construct capable of blocking, delaying or reducing the expression of JAK2 V617F in the animal. The method for producing said genetically modified animal is described in WO 04/022748 (Benitec).

Screening Methods

According to a fifth characteristic, the subject of the invention is a method for screening inhibitors specific to JAK2 V617F.

By "specific inhibitors" is meant compounds having a ratio of IC50 on JAK2/IC50 on JAK2 V617F of more than 5, 10, 25 or even 50. For example the compound has an IC50 on JAK2 V617F of less than 1 µM, preferably 100 nM, whereas it has an IC50 on JAK2 of more than 5 µM or 10 µM.

This method can be implemented using the protein of the invention, a membrane fraction containing said protein, a cell expressing said protein or a non-human transgenic animal such as described above.

Therefore, the invention relates to a test with which to determine the specific inhibition of JAK2 V617F by one or more compounds, comprising the steps consisting of contacting one or more compounds with the above-described JAK2 V617F protein, a membrane fraction containing JAK2 V617F or a cell expressing JAK2 V617F as described above under conditions suitable for fixing and detecting the specific fixation and/or inhibition of JAK2 V617F.

This method may also comprise measurement of the fixing onto wild-type JAK2.

This method may also consist of a succession of tests of several molecules and comprise a selection step to select molecules showing an IC50 for JAK V617F of less than 1 µM, preferably 100 nM.

This method may also comprise a negative selection step of the above-mentioned molecules which have an IC50 for JAK2 of less than 5 µM, or 1 µM.

The invention concerns in vitro screening such as described above in which immunoprecipitation is used to determine the inhibited phosphorylation of JAK2 V617F.

The invention also relates to in vivo screening on CD34-JAK2 V617F progenitor cells which are capable of differentiating without erythropoietin (Epo). Said cells are isolated from patients with Vaquez polyglobulia. The CD34-JAK2 V617F cells can be placed in culture in a medium containing SCF and IL-3. The compounds are added to the culture medium and the proliferating capacity of the cells is determined and their ability to differentiate into 36+/GPA- cells. The compounds selected are those for which a decrease in 36+/GPA-clones is observed. Hence, the invention relates to the above screening method using primary CD34+JAK V617F progenitor cells which are capable of differentiating without erythropoietin (Epo) or using cell lines which have become factor independent through the introduction of the JAK2 V617F variant. The same type of test can be conducted on marrow cultures of CFU-E type in a semi-solid medium with direct testing of the compound regarding the inhibition of spontaneous colony growth.

It is also possible to use any mammalian cell line described above expressing recombinant JAK V617F.

The invention also relates to a method for identifying candidate medicinal products, comprising the steps consisting of administering compounds to a non-human transgenic animal expressing JAK2 V617F such as described above, said animal reproducing Vaquez polyglobulia and/or having a myeloproliferative disorder associated with the presence of JAK2 V617F, of determining the effect of the compound and selecting candidate medicinal products which are seen to cause a reduction or blocking of proliferation and of spontaneous erythroblast differentiation in Vaquez polyglobulia or a reduction in cell proliferation associated with the presence of JAK2 V617F.

More particularly, this method is performed with a JAK2 V617F K-in mouse or JAK2 V617F K-in rat such as described above.

Among these compounds, mention may be made for example of siRNAs targeting the mutated exon 12 of JAK2 as described above, in particular siRNAs targeting sequence SEQ ID NO: 3, SEQ ID NO: 4, or SEQ ID NO: 11 comprising the mutated $t^{1849}$ nucleotide.

A further characteristic of the invention concerns the use of said above-described siRNAs or ddRNAi, and compounds specifically inhibiting JAK2 V617F to produce a medicinal product. Said medicinal product is particularly intended for the treatment of blood cancers, in particular myeloproliferative disorders including Vaquez polyglobulia, essential thrombocythaemia, myeloid splenomegaly or primitive myelofibrosis and chronic myeloid leukaemia. Said medicinal product is also intended for the treatment of other malignant hemopathies, associated with the JAK2 V617F mutation, and optionally solid tumours, carcinomas, melanomas and neuroblastomas which express JAK2 V617F.

For the remainder of the description and for the examples reference is made to the figures whose keys are described below:

BRIEF DESCRIPTION OF DRAWINGS

FIG. 2A—culture with Epo, SCF and IL-3
FIG. 2B—culture without Epo
FIGS. 5A-5B: Results of JAK2 inhibition in PV progenitors
    FIG. 5A—Reduction in the cloning capacity of 36+/gpa-.
        Culture D1-D6 in SCF-IL3, electroporation D5, sorting D6 (morpho/36/gpa-).
        Methyl SCF alone. Count on D13 (D7 post-sorting).
FIG. 5B—Structure of JAK2 with V617F mutation (exon 12).
FIGS. 6A and 6B: Detection of the mutation by the fusion analysis curve of LightCycler® with FRET hybridisation probes.
FIG. 6A: Experiments with various dilutions of HEL DNA in DNA TF-1 are shown. The peak JAK2 V617F(57°) is still detectable at a dilution of 1%.
FIG. 6B: Results of representative patient samples(#1: homozygous; #2: heterozygous; #3: weak; #4: non mutated).
FIG. 6C. Detection of the mutation by TaqMan® allele specific amplification. Experiments with dilution of HEL DNA (HEL 100 to 1%: empty squares; TF-1 cells: empty circles) and a few representative patient samples are shown (black crosses). #a: homozygous patients; #b: heterozygous patients; #c: weak patient; #d: non-mutated patients.
FIGS. 8 and 9: Expression of V617F Jak2 in HEL cells is reduced 24 hours after treatment with siRNA specific to JAX2 V617F Jak2 (siRNA #1, 3 and 4). siRNA # 1 corresponds to the sequence set forth in SEQ ID NO: 30, siRNA # 3 corresponds to the sequence set forth in SEQ ID NO: 29, and siRNA # 4 corresponds to the sequence set forth in SEQ ID NO: 31.
    0 to 6: HEL cells treated (1 to 6) or non-treated (0) with siRNA V617F Jak2.
    C+: 293HEK cells transfected with the V617F Jak2RV vector
    C-: 293 HEK

EXAMPLE 1

Figure 1:
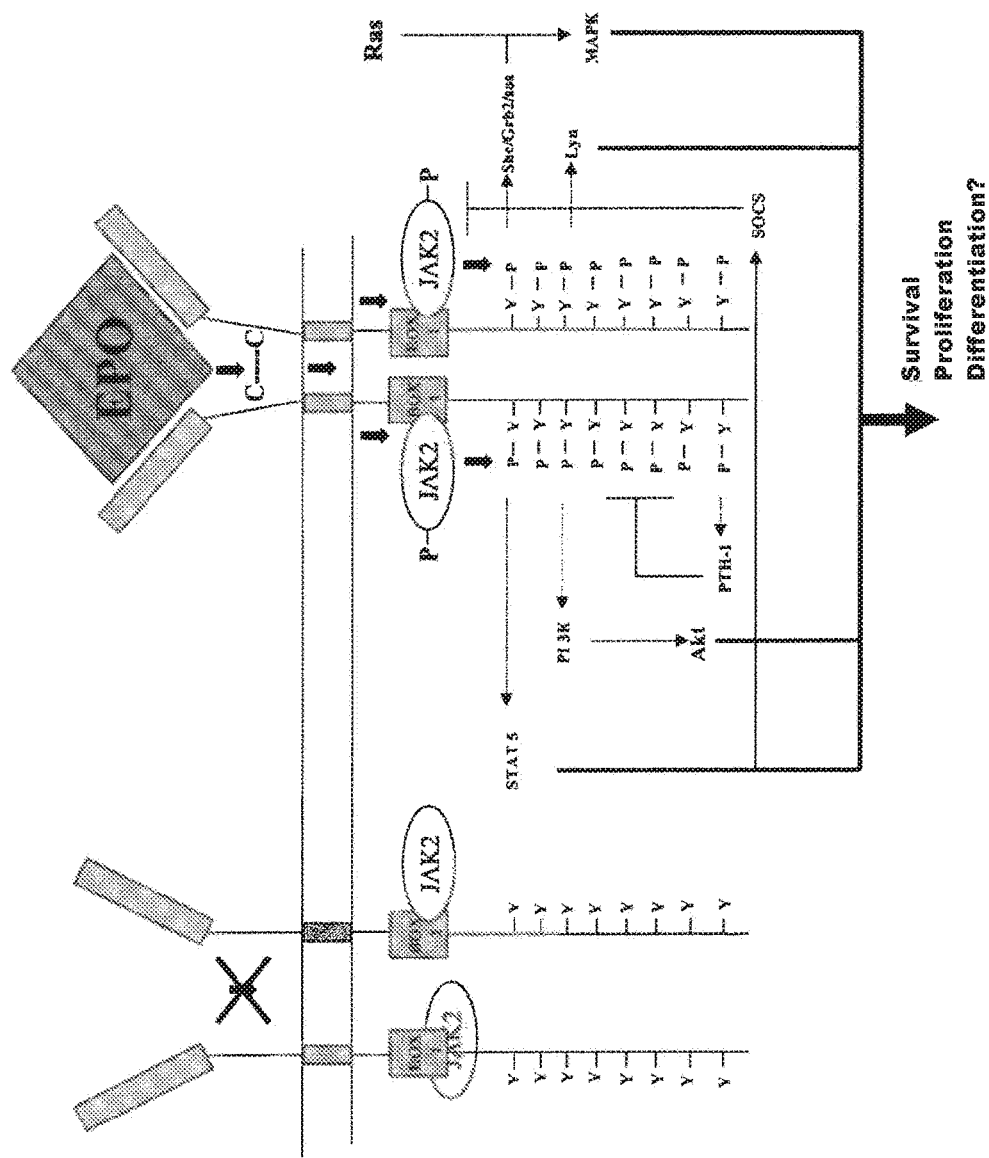
FIG. 1: Discovery of the key role of JAK2 in PV
In the basal state, JAK2 is fixed to box 1 in the non-phosphorylated state. The binding to Epo alters the conformation of the receptor and enables transphosphorylation of JAK2 which in return phosphorylates the intracytoplasmic residues of Epo-R thereby recruiting the different positive (->) or negative (-|) effectors of signal transduction.
Figure 2:
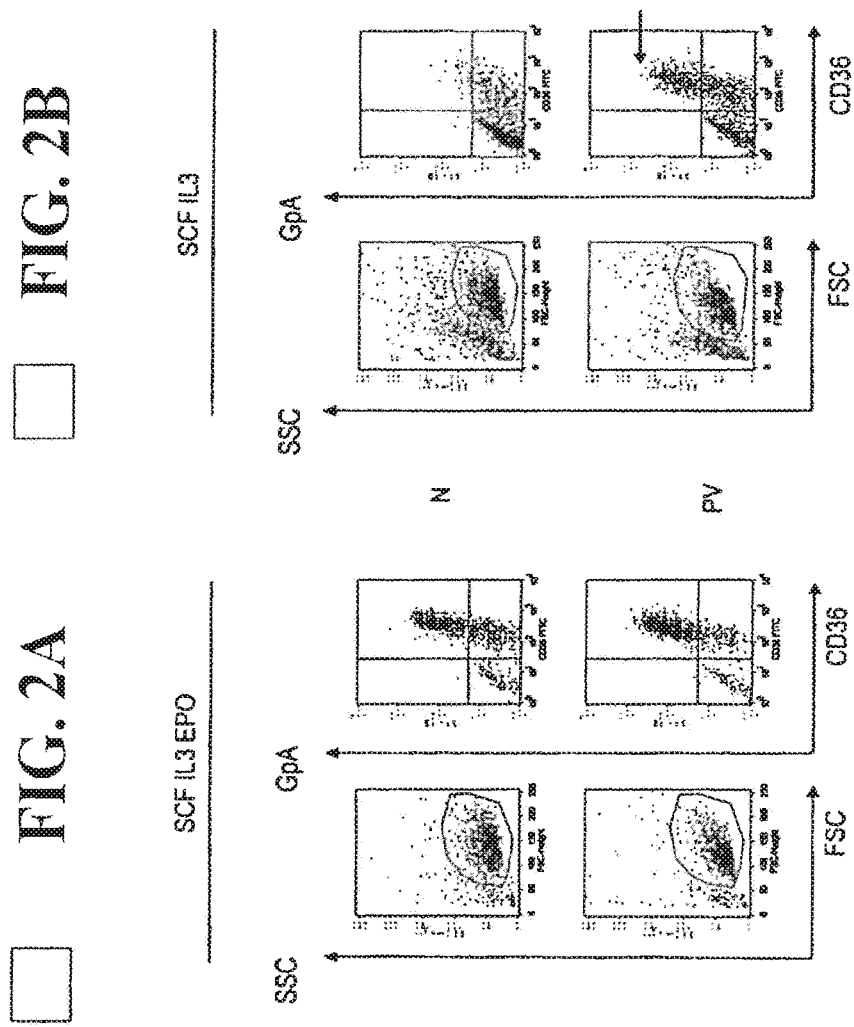
FIGS. 2A-2B: Design of a culture model of PV CD34+ progenitors that are erythropoietin-independent.
Figure 3:
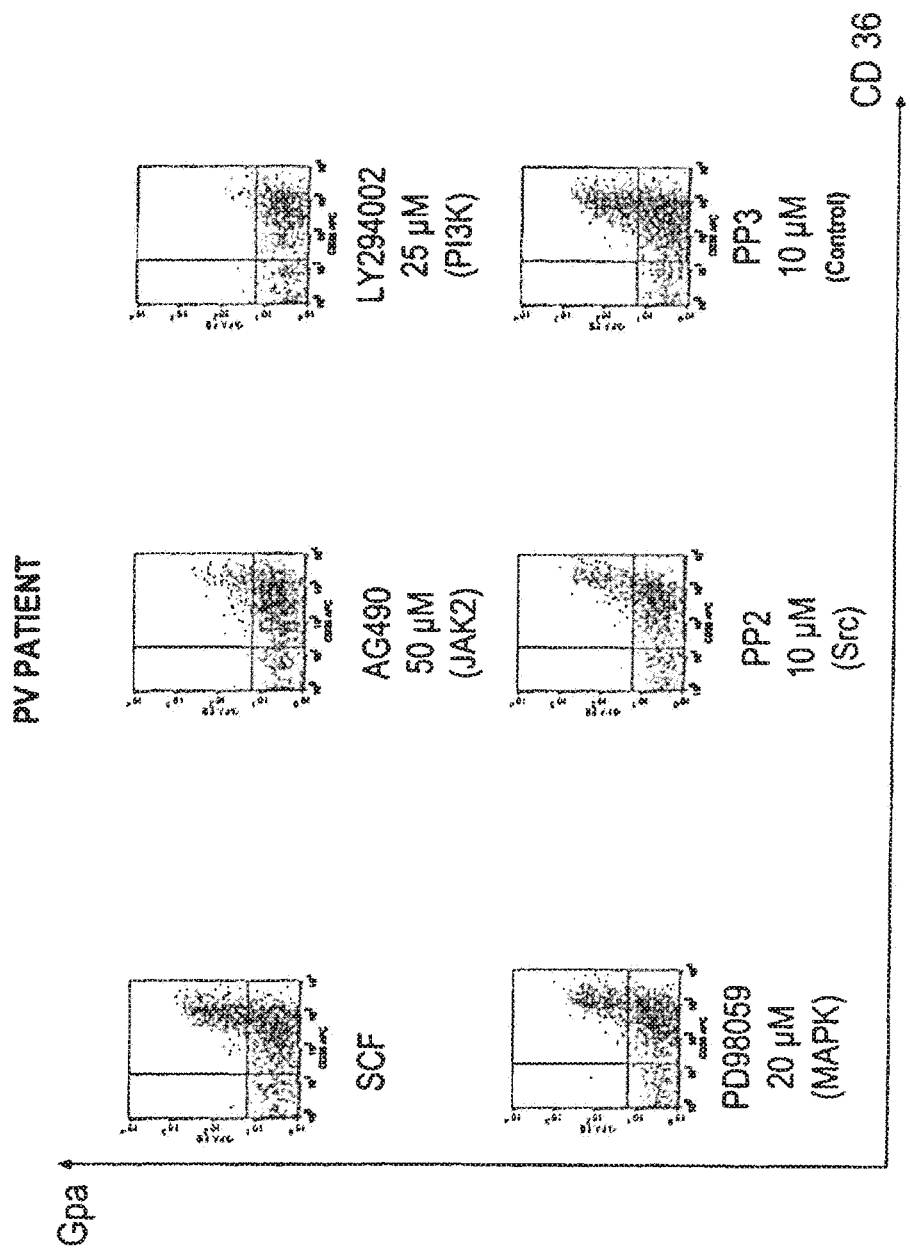
FIG. 3: Inhibition of JAK-STAT, Pi3-K and Src kinase pathways prevents spontaneous erythroid differentiation.
Figure 4:
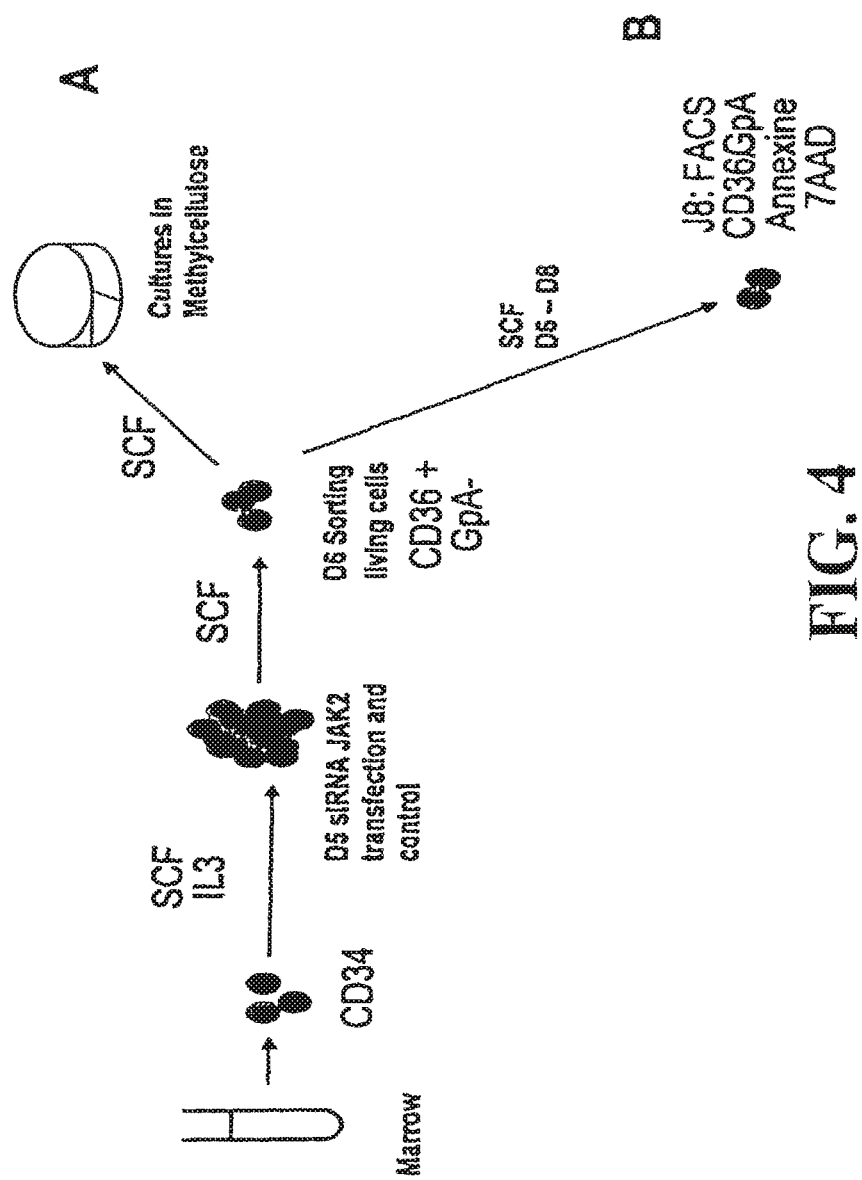
FIG. 4: Protocol for inhibiting JAK2 in PV progenitors

Identification of the JAK2 V617F Mutation in 39/43 Patients

The design of a cell culture model of pathological progenitors and the use of biochemical inhibitors enabled us to evidence that the JAK2-STAT5, P13 kinase and Src kinase pathways are necessary for Epo-independent differentiation of PV progenitors (Ugo et al 2004). These results reassured our hypothesis that the primary molecular lesion causing PV must be an anomaly of a key protein leading to deregulation of a signalling pathway, like the mutation of a tyrosine kinase imparting a constitutive activity. Nonetheless, it is the study of 43 patients suffering from Vaquez polyglobulia which made it possible to identify the key role played by the JAK2 protein which is the protein located the most upstream in these different signalling pathways, and which is common to the signalling pathways of cytokine receptors for which response anomalies have been described in PV. We examined the involvement of the JAK2 protein kinase in the physiopathology of PV taking three complementary approaches:
- a functional approach (inhibition of JAK2 in PV cells by interfering RNA)
- a genomic approach (sequencing of the 23 exons of the gene), and
- a biochemical approach to search a JAK2 phosphorylation anomaly, the cause of a constitutive activation.

The biological material used was derived from consenting patients suffering from polyglobulia and corresponds to residues of samples taken for diagnostic purposes and sent to the Hotel Dieu Central haematology laboratory, or to therapeutic phlebotomy.

1.1. Functional Study

Study of the JAK2 function in the erythroblasts of patients with Vaquez polyglobulia was conducted by using electroporation to transduce the PV erythroblasts with a siRNA specific to the JAK2 sequence (AMBION, Huntingdon, England) recognizing as target a sequence located on exon 15 of the mRNA of JAK2. We have shown that the inhibition of JAK2 strongly reduces the cloning capacity and "spontaneous" differentiation of PV progenitors in the absence of Epo. Normal erythroblast progenitors transfected with siRNA JAK2 show a reduction in clonogenic potential of 70% compared with the control siRNA, which confirms the efficacy of transfection with siRNA JAK2. In PV, the effects of JAK2 inhibition in the erythroblast progenitors were studied in an Epo-free culture model, making it possible to study the cells of the malignant clone. We compared the clonogenic potential, apoptosis and differentiation of the PV erythroblast progenitors after transfection with a siRNA JAK2 with respect to a control siRNA. Study of the clonogenic potential of PV progenitors cultured without Epo shows a very marked reduction in the number of colonies after transfection of siRNA JAK2 compared with control siRNA. Flow cytometry of the apoptosis of these cells shows a significant increase in the apoptosis of cells transfected with siRNA JAK2 compared with non-relevant siRNA (70 versus 53%). Study of the effects of siRNA JAK2 on differentiation (acquisition of Glycophorin A detected by flow cytometry) only shows a slight difference between the progenitors transfected with siRNA JAK2 versus control siRNA.

The results of the cell studies therefore showed that JAK2 is necessary for Epo-independent differentiation of PV erythroid progenitors. The initial results of biochemical studies (immunoprecipitation) show more extended phosphorylation of JAK2 after depriving PV erythroid progenitors of cytokines, as compared with normal cells.

1.2 Genomic Study of JAK2

PCR on the 23 exons was set up on a normal individual using genomic DNA. We then examined 3 patients suffering from PV after extracting the genomic DNA from erythroid cells obtained in vitro after cell culture.

We identified a point mutation located in exon 12 of JAK2, present in 2 out of the 3 patients tested. This mutation concerns base n° 1849 of the encoding sequence ([numbering starting at ATG], GenBank NM_004972) and transforms codon 617 of the JAK2 protein (V617F).

normal 617 codon: gtc code for a Valine (V)
mutated 617 codon: ttc code for a Phenylalanine(F)

Using the databases published on the Internet we were able to verify that it is not a known polymorphism.

We then widened the cohort. To date the mutation has been found in 39 patients with PV out of the 43 cases tested. No control (15 cases tested) or patient with secondary polyglobulia (18 cases tested) were found to carry the mutation.

Sequencing Results in Patients
- 39 mutated/43 PV tested (90%)
- 2/3 heterozygotes
- 13/39 "homozygotes" i.e. 30% of cases (same proportion as the loss of heterozygosity at 9p).

Controls
- 0 mutated cases out of 33 controls tested:
 - including 15 normal individuals
 - and 18 secondary polyglobulias (no spontaneous colonies).

The discovery of this anomaly of JAK2 accounts for the hypersensitivity to numerous growth factors involved in PV (Epo, TPO, IL-3, IL-6, GM-CSF, insulin). Indeed, JAK2 is a protein involved in the signalling pathways of the receptors of these cytokines.

Also, the association of JAK2 with R-Epo is particular in that JAK2 is fixed to E-Epo constitutively: the JAK2/R-Epo association initiated in the Golgi apparatus is necessary for the processing of R-Epo at the membrane of the erythroblasts. A JAK2 anomaly, the cause of modifications to the association of JAK2 with R-Epo, could therefore account for the medullary hyperplasia predominance on the erythroblast line, whereas this protein is involved in numerous signalling pathways. Also, Moliterno et al (Moliterno et al, 1998; Moliterno and Spivak, 1999) have evidenced faulty membrane expression of mpl related to a glycosylation defect. It is possible that JAK2, by analogy with R-Epo, is necessary for the processing of c-mpl. The anomaly of JAK2 could then explain the lack of membrane expression of c-mpl, found in PV.

JAK2 binds to R-Epo on its proximal domain, at a highly conserved domain, Box2. In the absence of Epo stimulation, JAK2 is constitutively fixed to R-Epo, but in a non-phosphorylated form, hence non-active. After stimulation of the receptor by Epo, the two JAK2 molecules phosphorylate, and then phosphorylate R-Epo enabling the recruitment then the phosphorylation of other proteins involved in signal transduction, such as the proteins STAT5, Grb2, P13K. The JAK2 protein, like all JAKs, has a functional kinase domain (JH1), a pseudo-kinase domain with no tyrosine kinase activity (JH2), and several conserved domains (JH3-JH7), characteristic of members of the JAK family. The JH2 domain appears to be involved in regulating the tyrosine-kinase activity of JAK2. According to available JAK2 protein mapping data (Lindauer, 2001), amino acid 617 is located in this JH2 domain and, following modelling studies, in a region of particular importance for the regulation of kinase activity.

Over and above the physiopathological interest of this discovery (understanding of the mechanisms of cytokine-independence, breakdown of the different SMPs) the evidencing of this mutation in a patient offers a test for the first time with which it is possible to confirm diagnosis. From a medical diagnosis viewpoint, the search for the mutation of JAK2 can be made on polynuclear neutrophils belonging to the malignant clone.

The invention also offers the determination of a specific treatment, of kinase inhibiting type specific to the mutated protein, or gene therapy.

EXAMPLE 2

Detection of the JAK2 V617F Mutant for First Intention Diagnosis of Erythrocytosis 2.1 Patients, Materials and Methods
Comparison Between Sequencing and Two Techniques of SNP Genotyping for the Detection of JAK2 V617F.
Patient Cells 119 samples of suspected MPD were analysed (i.e. erythrocytosis, thrombocytosis, hyperleukocytosis). 58 samples were taken for perspective analysis and 61 archive samples of bone marrow were analysed retrospectively.

The peripheral granulocytes were isolated using a density gradient method following the manufacturer's instructions (Eurobio, France). Mononuclear cells were isolated from the bone marrow using Ficoll density gradient centrifugation. The genomic DNA was extracted following standard procedures. To determine the sensitivity of LightCycler® and Taqman® technologies, the DNA derived from a homozygous sample with the allele of minimum residual wild type was diluted in series in normal DNA.
Cell Lines Serial solutions of DNA were used (1, 0.5, 0.1, 0.05, 0.01) from the human erythroleukaemia cell line (HEL) mutated homozygous fashion (JAK2 V617F) in DNA of TF-1 cell line (non-mutated) as standard positive controls. The cells lines grew in MEM-alpha medium (Invitrogen) enriched with foetal calf serum.
Detection of the Mutation by Analysis of the Fusion Curve of LightCycler® with FRET Hybridisation Probes.

Primers and probes were designed to amplify and hybridise to the target sequence of exon 12 of JAK2. The position of the mutation site (1849G/T) was covered with a donor capture probe labelled with fluoresceine at 3', and the adjacent acceptor anchor probe labelled with LightCycler® Red 640 (LCRed640) at its 5' end; its 3' end was phosphorylated to avoid extension. Amplification and analysis of the fusion curve were performed on the LightCycler® instrument (Roche Diagnostics, Meylan, France). The final reaction volume was 20 µl using 10 ng DNA, 14 µl LightCycler FastStart DNA Master mixture, 3 mM $MgCl_2$, 0.2 µM primers, 0.075 µM of each probe. In brief, the samples were heated to 95° C. for 10 minutes and PCR amplification of 45 cycles (10 seconds at 95° C., 10 seconds at 53° C., 15 seconds at 72° C.) was followed by a denaturing step at 95° C. for 10 seconds, two hybridisation steps at 63° C. and 45° C. for 30 seconds each and a fusion curve located in the domain lying between 45 and 70° C. (0.1° C./sec). Analysis on the LightCycler® programme was performed by plotting the curve of the fluorescence derivative with respect to temperature [2(dF12/F11)/dT) versus T]. The mutated peaks and WT were observed at 57 and 63° C. respectively.
Detection of the Mutation by Specific Amplification of an Allele Using TaqMan®.

Two primers were designed to amplify a product of 92 bp encompassing SNP at position 1849. Two fluorogenic MGB probes were designed with different fluorescent colourings, one targeted towards the WT allele, and one targeted towards the mutated allele. Genotyping was conducted in 96-well plates using the method based on Taqman® PCR. The final reaction volume was 12 µl using 10 ng genomic DNA, 6.25 µl TaqMan® Universal Master Mix and 0.31 µl 40X Assays-on-Demand SNP Genotyping Assay Mix (Applied Biosystems). The plate was heated to 95° C. for 10 minutes followed by 40 denaturation cycles at 92° C. for 15 seconds and matching/extension at 60° C. for 1 minute. Thermocycling was conducted on the 7500 Real Time PCR System (Applied Biosystems). Analysis was made using the SDS programme version 1.3. Genotyping of end point allele discrimination was performed by visual inspection of a fluorescence curve (Rn) derived from the WT probe against the Rn of the mutated JAK2 generated from post-PCR fluorescence reading.
Patients with Erythrocytosis and Sample Collection We evaluated 88 patients with hematocrit levels of more than 51%, at the time of diagnosis, before any form of treatment, and we studied the presence of WHO and PVSG criteria. The value of 51% was chosen for the upper end of the normal range for hematocrit level (Pearson T C et al, Polycythemia Vera Updated: Diagnosis, Pathobiology and Treatment. Hematology (AM. Soc. Hematol. Educ. Program.) 2000: 51 to 68). Bone marrow cells were collected for clonogenic asays and excess cells were collected for DNA extraction. Serum erythropoietin (Epo) was measured in different laboratories and it is therefore reported as being low when below the lower value of the normal domain in each laboratory, normal or high. The peripheral granulocytes derived from the same patients were purified as described previously, the blood samples of each time being available. The samples of bone marrow and blood were collected after receiving informed consent.
EEC Assays In vitro assays of erythroid Epo-response were all performed in the same laboratory (Hotel Dieu, Paris) using a plasma-clot culture technique as described previously (Casadevall N, Dupuy E, Molho-Sabatier P, Tobelem G, Varet B, Mayeux P. Autoantibodies against erythropoietin in a patient with pure red-cell aplasia. N. Engl. J. Med. 1996; 334: 630 to 633).
Statistical Analysis Correlation of the markers was made using the Spearman rank correlation coefficient (R).
2.2 Results
Feasibility and Sensitivity of Genotyping Techniques Based on PCR for Detection of the Mutation JAK2 V617F.

To assess the efficacy of sequencing, LightCycler® and Taqman® technologies for detection of the JAK2 V617F mutation, we searched its presence in 119 samples taken from patients suspected of having a MPD, using the 3 techniques in parallel. The JAK2 V617F mutation was efficiently detected in 83/119 samples, and 35 samples did not show the mutation with any of the 3 techniques. In only one sample, sequencing failed to detect the mutation revealed by the two technologies LightCycler® and Taqman® thereby suggesting that the latter may be more sensitive.

Figure 6A:
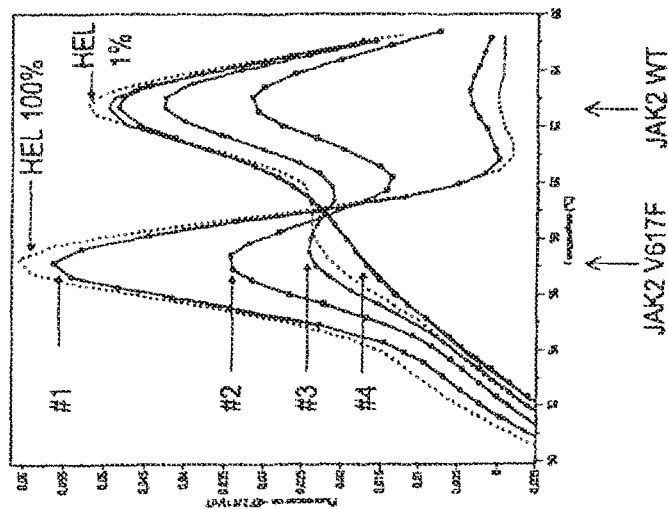
FIGS. 6A-6C: Genotyping analyses of SNPs to detect the JAK2 V617F mutation in genomic DNA using LightCycler® and TaqMan® technologies
Figure 6B:
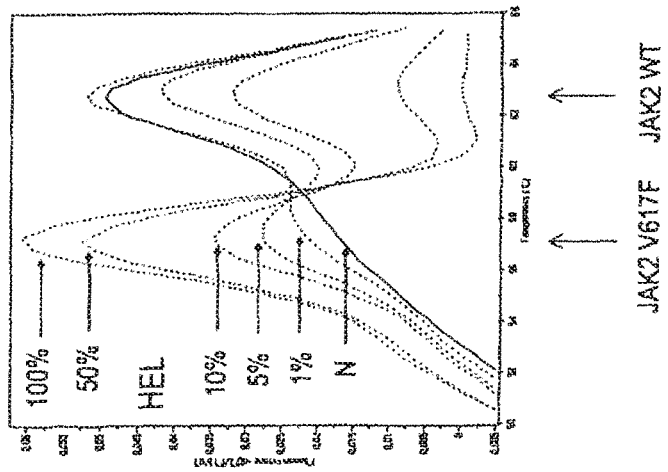
Figure 6C:
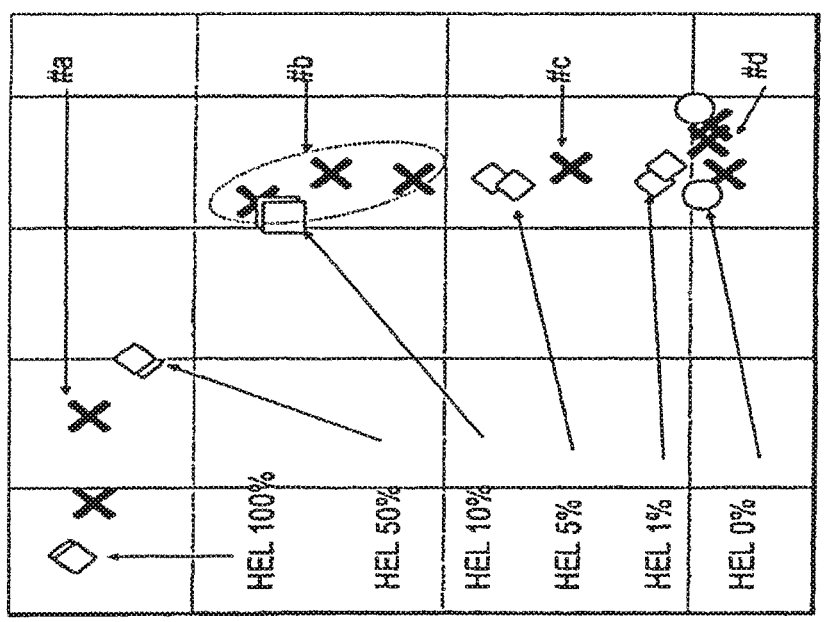

To assess the sensitivity of the technique, we used two different methods: we tested serial dilutions of DNA of the HEL cell line with homozygous mutation in the DNA of the non-mutated TF-1 cell line, and serial dilutions of the genomic DNA derived from a homozygous patient for the mutation JAK2 V617F in normal DNA. Sequencing failed to detect the mutated allele with 5% DNA of the HEL cell line diluted in the DNA of the TF-1 cell line, and with 10% of the DNA from the patient with homozygous mutation diluted in normal DNA. The sensitivity of the LightCycler® and Taqman® techniques was equivalent, slightly better than sequencing, reaching 0.5 to 1% of the DNA from the HEL cell line diluted in the DNA of the TF-1 cell line (FIG. 6) and 2 to 4% of the DNA from a patient with homozygous mutation diluted in normal DNA.

Characteristics of Patients with Erythrocytosis at the Time of Diagnosis

The chief characteristics of 88 patients with hematocrit levels of more than 51% at the time of diagnosis are summarized in Table I.

cell mass). The clinical data were incomplete for 7 patients, accounting for the fact that PV diagnosis could not be confirmed either with WHO criteria or with PVSG criteria. On account of the difference between the AI criteria of the two classifications, 6 patients who had no red cell mass measurement could be classified in the WHO classification but not in the PVSG classification. One patient showed both hypoxia and EEC formation, thereby making diagnosis difficult. Cytogenetic analysis was performed in 35 patients; among 32 PV patients (WHO criteria) 7 showed cytogenetic anomalies: 5 with trisomy 9, 1 with 7q- and 1 with additional material on chromosome 18.

The Presence of JAK2 V617F Corresponds to PVSG and WHO Criteria for PV

JAK2 V617F was present in 43/45 (96%) of patients diagnosed with PV in accordance with PVSG criteria and in 57/61 (93%) of patients diagnosed using WHO criteria (Table I). Nonetheless, 8/29 patients classified as non-PV according to PVSG criteria showed the mutation, but none of the 19 WHO non-PV patients; these 8 patients were

TABLE 1

Patient Characteristics

| | WHO criterion | | PVSG criterion | | WHO and PVSG criteria | |
|---|---|---|---|---|---|---|
| | PV<br>n = 61 | Idiopathic erythrocytosis<br>n = 11 | PV<br>n = 45 | Idiopathic erythrocytosis<br>n = 21 | Secondary erythrocytosis<br>n = 5 | Hct > 50% but no AE<br>n = 3 |
| Sex ratio (male/female) | 38/23 | 11/0 | 28/17 | 18/3 | 4/1 | 3/0 |
| Mean age (domain) | 61 (23 to 92) | 57 (24 to 81) | 58 (23 to 92) | 60 (53 to 81) | 65 (55 to 77) | 48.6 |
| mean Ht (%) ± σ | 59 ± 4.6 | 54.6 ± 1.44 | 59.2 ± 4.5 | 57.8 ± 4.2 | 55.8 ± 3.1 | 53.3 ± 0.8 |
| Mean Hb (g/dL) ± σ | 19.2 ± 1.39 | 18.3 ± 0.34 | 19.3 ± 1.41 | 19 ± 1.0 | 18.9 ± 0.8 | 18.6 ± 0.5 |
| Mean WBC ($\times 10^9$) ± σ | 12.2 ± 4.4 | 7.0 ± 2.5 | 13.5 ± 4.9 | 8.2 ± 2.5 | 8.8 ± 1.9 | 6.6 ± 0.4 |
| Mean platelet count ($\times 10^9$) ± σ | 463 ± 148 | 212 ± 38 | 503 ± 149 | 245 ± 60.4 | 212 ± 29 | 175 ± 19 |
| Splenomegalia | 16/55 | 0/11 | 14/39 | 0/21 | 0/5 | 0/3 |
| EEC presence | 59/60 | 1/11 | 43/44 | 11/21 | 0/5 | 0/3 |
| Low Epo level | 39/47 | 2/8 | 27/33 | 10/17 | 0/3 | 1/1 |
| Normal Epo level | 8/47 | 6/8 | 6/33 | 7/17 | 3/3 | 0/1 |
| Cytogenetic anomalies | 7/32 | 0/3 | 6/23 | 0/7 | nd | 0/1 |
| Positive JAK2V617F | 57/61 | 0/11 | 43/45 | 8/21 | 0/5 | 0/3 |

88 patients with hematocrit levels of over 51% were diagnosed in accordance with PVSG and WHO criteria into four groups: Vaquez disease (PV), idiopathic erythrocytosis, secondary erythrocytosis and "no absolute erythrocytosis" (no AE) when measured red cell mass had not increased. 8 patients could not have any definite diagnosis since some clinical data were not available. Hct: hematocrit; Hb: haemoglobin; WBC: white blood cells; EEC: endogenous erythroid colonies; Epo: erythropoietin; σ: standard deviation. The patients could be divided into 4 main groups in accordance with WHO criteria (Pierre R et al, editors, World Health Organization Classification of Tumours; Pathology and Genetics of tumours of hematopoietic and lymphoid tissues. Lyon; IARC Press: 2001: to 34) and PVSG criteria (Pearson T C, Messinezy M. The diagnostic criteria of polycythaemia *rubra* vera. Leuk Lymphoma 1996; 22 Suppl 1:87 to 93): 61 and 45 patients with PV diagnosis, 5 with secondary erythrocytosis, 11 and 21 with idiopathic erythrocytosis and 3 with no absolute erythrocytosis (normal red cell mass).

considered IE with PVSG criteria and PV with WHO criteria. None of the patients diagnosed with SE nor the patient with normal red cell mass ("no AE") had the mutation. The presence or absence of JAK2 V617F therefore corresponds to positive PV diagnosis in 76/80 patients (95% R=0.879, p<0.0001) with WHO criteria, and in 64/74 patients (86.5%, R=0.717, p<0.0001) with PVSG criteria. In addition, since none of the patients diagnosed as non-PV according to WHO criteria showed the mutation, the detection of JAK2 V617F has a 100% predictive value in the context of absolute erythrocytosis.

Some authors (Mossuz P et al, Diagnostic value of serum erythropoietin level in patients with absolute erythrocytosis. Haematologica 2004; 89: 1194 to 1198) consider the measurement of serum erythropoietin level as a first intention diagnostic test for patients with absolute erythrocytosis, with a specificity of 97%, and a predictive value of 97.8% for diagnosis of PV if the Epo level is below the lower value of the normal range. In our study, the correlation between the Epo level and PV diagnosis according to WHO and PVSG criteria was respectively observed in 50/61 (82%, R=0.488, p=0.0002) and 39/56 (70%, R=0.358, p=0.0067) patients. We then compared the serum Epo level in the presence or absence of V617F JAK2 and it was found that 52/68 patients (76%, R=0.416, p=0.0004) showed adequate correlation.

The presence of the JAK2 V617F mutation corresponds to the capacity for forming EECs.

Three different teams have shown that Epo-dependent cell lines transfected with JAK2 V617F were Epo-independent and Epo-hypersensitive for their growth, thereby mimicking the independence and hypersensitivity of the erythroid progenitors described in PV. Therefore, we have put forward the hypothesis that patients carrying JAK2 V617F also showed EEC formation. Among the 20 patients with erythrocytosis with no EEC formation, one showed the mutation, raising the query of the positive predictive value of JAK2 V617F detection; however, even if this patient showed no EEC, he/she met the numerous WHO and PVSG positive criteria allowing the patient's classification as PV in both classifications. This patient should therefore be considered a "false-negative to EEC" rather than a "false-positive for JAK2". Among the 67 patients who had EEC formation, 62 carried the JAK2 V617F mutation, 5 patients not being mutated using detection-sensitive techniques. Among these 5 patients, 4/5 and 2/5 could be classified in the PV group according to WHO and PVSG criteria respectively. Overall, out of the 87 analysed patients, the presence or absence of the JAK2 V617F mutation corresponded to the capacity or incapacity to form EECs in 81/87 patients (93.1%, R=0.824, p<0.0001).

The presence of the JAK2 V617F mutation in bone marrow mononuclear cells (BMMC) corresponds to its presence in the peripheral granulocytes.

To examine whether the use of granulocytes of peripheral blood to detect JAK2 V617F mutation at the time of diagnosis could avoid the assay of bone marrow cells, we compared the results obtained by each of the methods: sequencing, LightCycler® and TaqMan®, in 50 patients (including 35 PV, 8 SE and 8 suspected MPD) for whom both bone marrow samples and peripheral blood samples were available at the time of diagnosis. In all cases (34 mutated, 16 non-mutated) mutation was identically detected.

III—Conclusion

Figure 7:
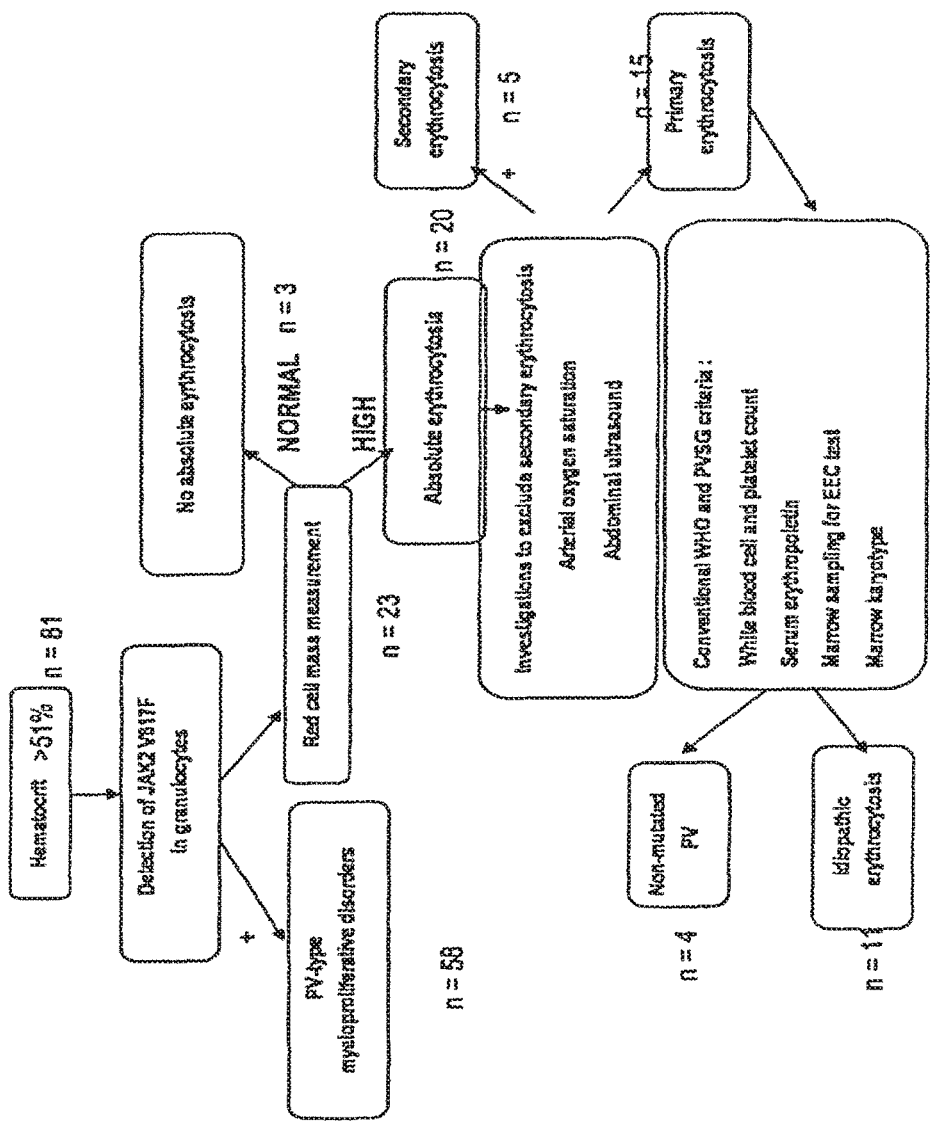
FIG. 7: Proposed diagnostic datasheet to diagnose erythrocytosis (i.e. hematocrit level over 51%).
    The number of patients concerned at each stage of the datasheet is written next to each item (n), only those patients showing all clinical data being listed here (n=81). Detection of JAK2 V617F as a first intention diagnostic test would have prevented 58/81 patients from undergoing other investigations to diagnose a PV type myeloproliferative disorder.

We therefore propose a new PV diagnosis datasheet in which the detection of JAK2 V617F in the granulocytes using sensitive techniques is the first step in the diagnosis of erythrocytosis, except in the case of obvious secondary erythrocytosis (FIG. 7). This approach has several advantages: it avoids having to conduct measurement of isotopic red blood cells, which is not always available and whose result is sometimes subject to debate. It can also avoid bone marrow procedure and EEC assays which are time-consuming and are not well standardized. It drastically reduces the cost of positive PV diagnosis, since only those patients with hematocrit levels of over 51% and who are JAK2 V617F negative need to undergo all the investigations which are actually carried to characterize an erythrocytosis. Even if the detection alone of JAK2 V617F in an erythrocytosis context will support PV diagnosis, performing a bone marrow biopsy may still be useful since it may reveal signs of myelofibrosis or the presence of blastic cells, thereby confirming the leukaemic transformation of PV. Nonetheless, we feel that a bone marrow biopsy should be performed for optional study with cytogenetic analysis.

JAK2 V617F was also detected in 30% of ET, 50% of IMF and a few rare non-characterized MPDs, thereby defining a new MPD group with different clinical signs. The reasons for these differences remain unknown and it is still too early to group these diseases into a single myeloproliferative entity with a common physiopathological cause and different phenotypes. Subsequent precise clinical studies would characterize more specifically the common signs between PV, ET, IMF and other rare MPDs carrying JAK2 V617F, especially in terms of absolute erythrocytosis, Epo level, myelofibrosis and cytogenetic anomalies. It is therefore contemplated to use the detection of JAK2 V617F as an initial tool for the diagnosis of chronic hyperleukocytosis, thrombocytosis and erythrocytosis. The presence of JAK2 V617F will not only allow a new definition of a MPD group, but it will also most certainly form the basis for developing specific targeted therapies.

EXAMPLE 3 siRNAs Specific to the V617F JAK2 Mutation Inhibit V617F JAK2 but not JAK2 WT

Figure 9:
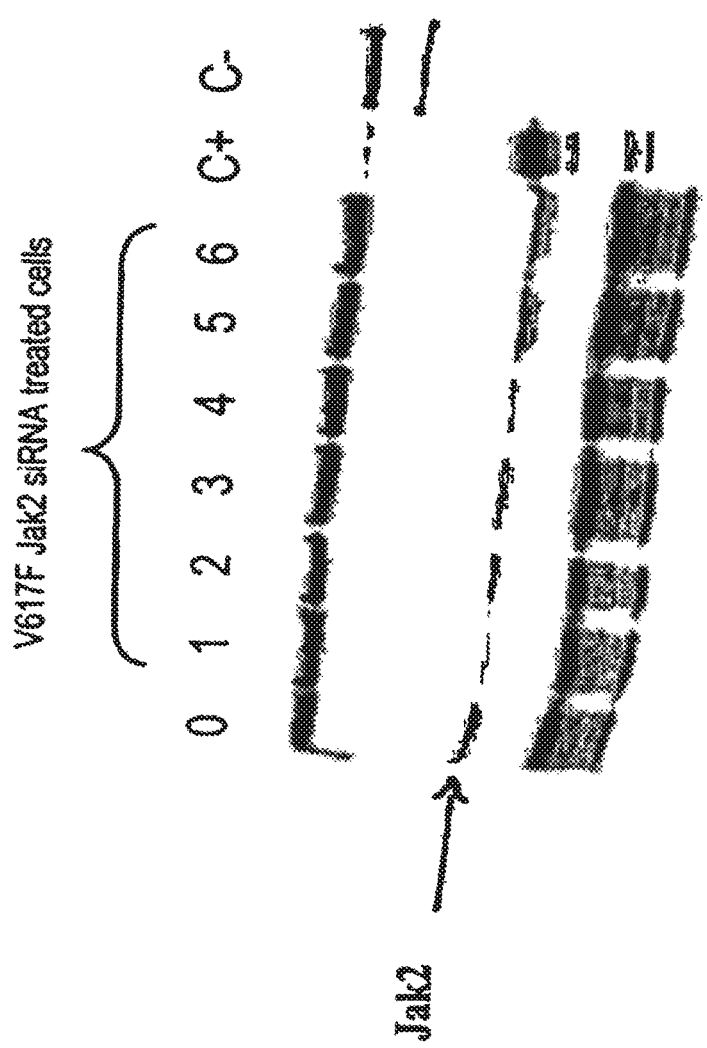
Figure 10:
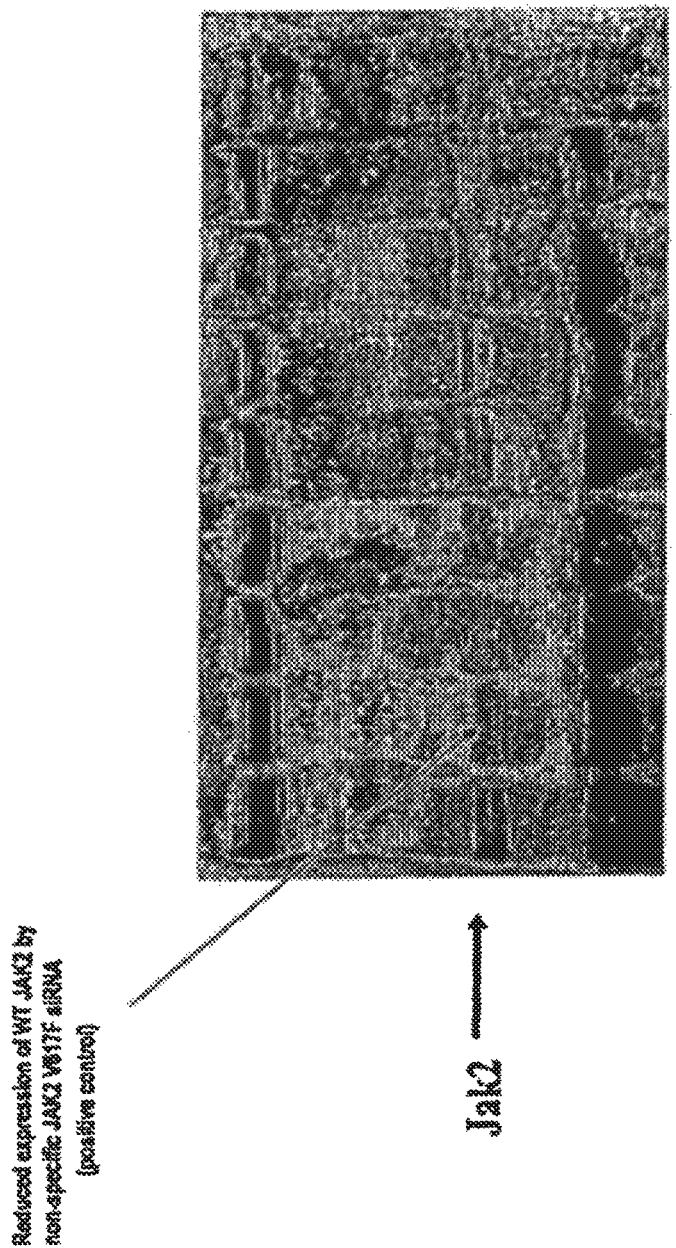
FIG. 10: Level of WT Jak2 expression in K562 cells remains unchanged 24 hours after treatment with siRNA specific to Jak2 V617.
    Je: K562 cells treated with siRNA WT Jak2
    0 to 6: K562 cells treated with siRNA V617F Jak2
    C-: 293HEK (no expression of JAK2).

The siRNAs 1, 3 and 4 corresponding to sequences SEQ ID NO 25 to 27 inhibit the mutated protein V617F JAK2 expressed by the HEL line without inhibiting the wild-type JAK2 protein expressed by the K562 line. The results are shown FIGS. 8, 9 and 10.

REFERENCES

Andersson P, LeBlanc K, Eriksson B A and Samuelsson J (1997). No evidence for an altered mRNA expression or protein level of haemopoietic cell phosphatase in CD34+ bone marrow progenitor cells or mature peripheral blood cells in polycythaemia vera. Eur J Haematol 59, 310-7.

Asimakopoulos F A, Hinshelwood S, Gilbert J G, Delibrias C C, Gottgens B, Fearon D T and Green A R (1997). The gene encoding hematopoietic cell phosphatase (SHP-1) is structurally and transcriptionally intact in polycythemia vera. Oncogene 14, 1215-22.

Casadevall N, Vainchenker W, Lacome C, Vinci J, Chapman J, Breton-Gorins J and Varet B (1982). Erythroid progenitors in Polycythemia Vera. Demonstration of their hypersensitivity to erythropoietin using serum-free cultures. Blood 59, 447-451.

Hess G, Rose P, Gamm H, Papadileris S, Huber C and Seliger B (1994). Molecular analysis of the erythropoetin receptor system in patients with polycythaemia vera. Br J Haematol 88, 794-802.

Kralovics R, Guan Y and Prchal J T (2002). Acquired uniparental disomy of chromosome 9p is a frequent stem cell defect in polycythaemia vera. Exp Hematol 30, 229-36.

Le Couedic J P, Mitjavila M T, Villeval J L, Feger F, Gobert S, Mayeux P, Casadevall N and Vainchenker W (1996). Missense mutation of the erythropoietin receptor is a rare event in human erythroid malignancies. Blood 87, 1502-11.

Lindauer K, Loerting T, Liedl K R, and Kroemer R T (2001). Prediction of the structure of human Janus kinase 2 (JAK2) comprising the two carboxy-terminal domains reveals a mechanism for autoregulation. Protein Eng 14, 27-37.

Means R T, Krantz S B, Sawyer S and Gilbert H (1989). Erythropoietin receptors in polycythemia vera. J Clin Invest 84, 1340.

Moliterno A R, Hankins W D and Spivak Jl (1998). Impaired expression of the thrombopoietin receptor by platelets from patients with Polycythemia Vera. N Engl J Med 338, 572-580.

Moliterno A R and Spivak J L (1999). Posttranslational processing of the thrombopoietin receptor is impaired in polycythemia vera. Blood 94, 2555-61.

Pahl H L (2000). Towards a molecular understanding of polycythemia *rubra* vera. Eur J Biochem 267, 3395-401.

Pearson (2001). Evaluation of diagnostic criteria in polycythemia vera. Semin Hematol 38, 21-4.

Roder S S C, Meinhardt G, Pahl H L (2001). STAT3 is constitutively active in some patients with Polycythemia *rubra* vera. Exp Hematol 29, 694-702.

Silva M, Richard C, Benito A, Sanz C, Olalla I and Fernandez-Luna J L (1998). Expression of Bcl-x in erythroid precursors from patients with polycythemia vera. N Engl J Med 338, 564-71.

Temerinac S, Klippel S, Strunck E, Roder S, Lubbert M, Lange W, Azemar M, Meinhardt G, Schaefer H E and Pahl H L (2000). Cloning of PRV-1, a novel member of the uPAR receptor superfamily, which is overexpressed in polycythemia *rubra* vera. Blood 95, 2569-76.

Ugo V, Marzac C, Teyssandier I, Larbret F, Lécluse Y, Debili N, Vainchenker W and Casadevall N (2004). Multiple signalling pathways are involved in erythropoietin-independent differentiation of erythroid progenitors in Polycythemia Vera. Experimental Hematology 32, 179-187.

What is claimed is:

1. A method for detecting a mutation in the JAK2 (Janus kinase 2) gene of a human patient, comprising:
  detecting a thymine (T) in the JAK2 gene at position 2343 of SEQ ID NO: 2 in a human nucleic acid sample by:
   a) sequencing a region of the nucleic acid sample comprising position 2343 of SEQ ID NO: 2, or
   b) hybridizing the nucleic acid sample with at least one probe or primer comprising at least 10 consecutive nucleotides of SEQ ID NO: 2 comprising position 2343 of SEQ ID NO: 2, or with a complement of said probe or primer.

2. The method of claim 1, wherein the at least one probe is labeled with at least one marker and detecting comprises detection of a signal produced by the at least one probe.

3. The method of claim 1, wherein the hybridizing comprises hybridizing with at least two probes.

* * * * *